US006579326B2

(12) United States Patent
Breton et al.

(10) Patent No.: US 6,579,326 B2
(45) Date of Patent: *Jun. 17, 2003

(54) COMPOSITIONS FOR DYEING KERATIN FIBERS, CONTAINING CATIONIC INDOLIZINE DERIVATIVES, AND DYEING PROCESS

(75) Inventors: Philippe Breton, Le Chesnay (FR); Fabienne Segala, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/791,822

(22) Filed: Feb. 26, 2001

(65) Prior Publication Data

US 2003/0028975 A9 Feb. 13, 2003

(30) Foreign Application Priority Data

Feb. 25, 2000 (FR) ............................................ 00 02419

(51) Int. Cl.⁷ ................................................. A61K 7/13
(52) U.S. Cl. ....................... 8/405; 8/406; 8/407; 8/408; 8/409; 8/410; 8/412; 546/85
(58) Field of Search ............................ 8/405, 406, 407, 8/408, 409, 410, 412; 546/85

(56) References Cited

U.S. PATENT DOCUMENTS

| | | | |
|---|---|---|---|
| 3,260,601 A | 7/1966 | Bailey | 96/84 |
| 3,642,807 A | 2/1972 | Walter | 260/296 B |
| 3,717,644 A | 2/1973 | Walter | 260/293.52 |
| 3,846,131 A | 11/1974 | Lohmann et al. | 96/48 R |
| 4,003,699 A | 1/1977 | Rose et al. | 8/10.2 |
| 4,013,404 A | 3/1977 | Parent et al. | 8/11 |
| 4,168,953 A | 9/1979 | Rose | 8/10.2 |
| 4,275,206 A | 6/1981 | Becker et al. | 546/115 |
| 4,400,387 A | 8/1983 | Rosseels et al. | 424/263 |
| 4,823,985 A | 4/1989 | Grollier et al. | 222/1 |
| 5,061,289 A | 10/1991 | Clausen et al. | 8/405 |
| 5,380,340 A | 1/1995 | Neunhoeffer et al. | 8/409 |
| 5,686,084 A | 11/1997 | Wenke et al. | 424/401 |
| 5,766,576 A | 6/1998 | Löwe et al. | 424/62 |
| 6,099,593 A | 8/2000 | Terranova et al. | 8/409 |

FOREIGN PATENT DOCUMENTS

| | | |
|---|---|---|
| DE | 464481 | 8/1928 |
| DE | 1 492 166 | 12/1969 |
| DE | 23 59 399 | 6/1975 |
| DE | 26 23 564 | 12/1977 |
| DE | 38 43 892 | 6/1990 |
| DE | 41 33 957 | 4/1993 |
| DE | 195 43 988 | 5/1997 |
| EP | 0 989 128 | 3/2000 |
| FR | 2 586 913 | 3/1987 |
| FR | 2 733 749 | 11/1996 |
| FR | 2 750 048 | 12/1997 |
| GB | 1 026 978 | 4/1966 |
| GB | 1 153 196 | 5/1969 |
| GB | 1 174 124 | 12/1969 |
| GB | 2075540 | 11/1981 |
| JP | 2-19576 | 1/1990 |
| JP | 9-110659 | 4/1997 |
| WO | WO 94/08969 | 4/1994 |
| WO | WO 94/08970 | 4/1994 |
| WO | WO 96/15765 | 5/1996 |
| WO | WO 99/15137 | 4/1999 |

OTHER PUBLICATIONS

A.E. Tschitschibabin, "Tautomerie in der Pyridin–Reihe", Berichte der Deutschen Chemischen Gesellschaft, vol. 60, No. 7, Jul. 13, 1927, pp. 1607–1617.

Luciano Pentimalli et al., "Reattività di Azaindeni, Nota III. Piridiletilazione e Aoiletilazione di Indolizine", Annali di Chimica, vol. 56, No. 6, 1966, pp. 752–758.

E.T. Borrows et al., "The Chemistry of the Pyrrocolines. Part I. 2–Methyl– and 2–Phenyl–pyrrocoline", Journal of The Chemical Society, Jan. 1946, pp. 1069–1075.

Takane Uchida et al., "Methods for the Construction of the Indolizine Nucleus", International Journal of Methods in Synthetic Organic Chemistry, No. 4, Apr. 1976, pp. 209–236.

Co–pending application—Attorney Docket No. 05725.0859–00000 Title: Indolizine Derivatives, Compositions Comprising at Least One Coupler Chosen from Indolizine Derivatives and at Least One Oxidation Base, and Methods for Using Same Inventor(s): Philippe Breton et al. U.S. Filing Date: Feb. 26, 2001.

Chemical Abstracts, vol. 65, No. 9, 1966, Abstract No. 13652, XP–002155705.

English language Derwent Abstract of DE 1 492 166. Dec. 1969.

English language Derwent Abstract of EP 0 989 128. Mar. 2000.

(List continued on next page.)

Primary Examiner—Yogendra N. Gupta
Assistant Examiner—Eisa Elhilo
(74) Attorney, Agent, or Firm—Finnegan, Henderson, Farabow, Garrett & Dunner, LLP

(57) ABSTRACT

Compositions for the oxidation dyeing of keratin fibers, containing at least one oxidation base and at least one coupler chosen from indolizine derivative comprising at least one cationic group Z, Z being chosen from quaternized aliphatic chains, aliphatic chains comprising at least one quaternized saturated ring, and aliphatic chains comprising at least one quaternized unsaturated ring. Methods of using these cationic indolizine derivatives as couplers for the oxidation dyeing of keratin fibers, in combination with at least one oxidation base, and to dyeing processes using them. Some of these cationic indolizine derivatives are novel.

61 Claims, No Drawings

OTHER PUBLICATIONS

English language Derwent Abstract of FR 2 733 749. Nov. 1996.

English language Derwent Abstract of JP 2-19576. Jan. 1990.

English language Derwent Abstract of JP 9-110659. Apr. 1997.

Chemical Abstract: "Cyanine dyes from 2-phenylindoliziines"; Russian Abstract No. 7Zh382, XP-002178582. 1969.

D. Lide et al: "CRC Handbook of Chemistry and Physics," 76th ed., p. 3-201, compound 7324, XP-002178581. No Date.

J. Hickman et al.: "Indolizines. Part V. The synthesis of 3-amino and 3-acetamido-indolizines and their precursors, the 3-azo-, -nitroso-, -nitro-, and -acetyl-indolizines," J. Chem. Soc., Perkin Trans. I, No. 23, 1972, pp. 2954-2958, XP-001024447.

R. Bonneau et al.: "Synthesis of 3-substituted Indolizines from the Reaction of Chlorocarbenes with 2-vinylpyridine," J. Chem Soc., Chem. Commun., vol. 4, 1994, pp. 509-510, XP-001024448.

COMPOSITIONS FOR DYEING KERATIN FIBERS, CONTAINING CATIONIC INDOLIZINE DERIVATIVES, AND DYEING PROCESS

The invention relates to compositions for the oxidation dyeing of keratin fibres, comprising at least one oxidation base and at least one coupler chosen from indolizine derivatives comprising at least one cationic group Z, wherein Z may be chosen from quaternized aliphatic chains, aliphatic chains comprising at least one quaternized saturated ring, and aliphatic chains comprising at least one quaternized unsaturated ring, to oxidation dyeing processes using them and to novel cationic indolizine derivatives.

Dye compositions comprising oxidation dye precursors are known in the art for dyeing keratinous fibres, such as human hair. The oxidation dye precursors include ortho-phenylenediamines, para-phenylenediamines, ortho-aminophenols, para-aminophenols, and heterocyclic compounds. These are generally known as oxidation bases. The oxidation dye precursors, i.e., oxidation bases, are generally colorless or weakly colored compounds which may give rise to colored compounds and dyes when combined with oxidizing products via oxidative coupling.

The shades obtained with these oxidation bases may be varied by combining them with couplers or coloration modifiers. Such coloration modifiers may, for example, be chosen from aromatic meta-diamines, meta-aminophenols, meta-diphenols, and certain heterocyclic compounds, such as indole compounds.

The variety of molecules used as oxidation bases and couplers may make it possible to obtain a wide range of colours.

The so-called "permanent" coloration obtained from using these oxidation dyes should have at least one of the following desirable characteristics. The coloration should have no toxicological drawbacks, the shades obtained should have the desired intensity, and the coloration should have good resistance to external agents to which the fibres may be subjected, such as light, bad weather, washing, permanent-waving, perspiration, and rubbing. The dyes should allow coverage of white hairs, and should be as unselective as possible, that is, they should allow only the smallest possible differences in coloration along the same keratin fiber, which may be differently sensitized (i.e. damaged) between its end tip and its root.

Indazole-type compounds have been used in the field of hair dyeing. For example, in DE-A-1 492 166, the disclosure of which is incorporated herein by reference, the polycondensation of such compounds via oxidation has been proposed; in DE-A-2 623 564, the disclosure of which is incorporated herein by reference, it has been proposed to combine hydroxy-indazoles with tetraaminopyrimidines, and in U.S. Pat. No. 4,013,404, the disclosure of which is incorporated herein by reference, certain aminoindazoles and their use as oxidation dye precursors have been proposed.

The inventors have discovered, entirely surprisingly and unexpectedly, that the indolizine derivatives of formula (I) defined below comprising at least one cationic group Z, Z being chosen from quaternized aliphatic chains, aliphatic chains comprising at least one quaternized saturated ring and aliphatic chains comprising at least one quaternized unsaturated ring, are not only suitable for use as couplers for oxidation dyeing, but also make it possible to obtain dye compositions which provide at least one of intense colorations in a very wide range of shades and excellent properties of resistance to the various treatments to which the keratin fibres may be subjected.

A subject of the invention is thus a composition for dyeing keratin fibres, such as, for example, human keratin fibres such as the hair, wherein the composition comprises, in a medium which is suitable for dyeing:

(i) at least one oxidation base; and (ii) at least one coupler chosen from indolizine derivatives of formula (I) and the acid addition salts thereof:

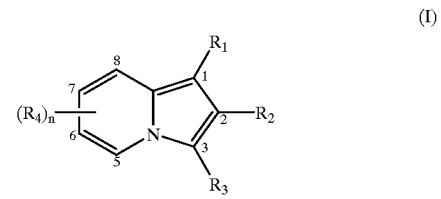

in which:

n may be an integer from 0 to 4;

$R_1$ and $R_3$, which may be identical or different, are each chosen from hydrogen atoms; halogen atoms; Z groups; $C_1$–$C_4$ alkyl radicals; $C_1$–$C_4$ alkoxy radicals; $C_1$–$C_4$ monohydroxyalkyl radicals; $C_2$–$C_4$ polyhydroxyalkyl radicals; $C_1$–$C_4$ aminoalkyl radicals; acetylamino radicals; acetylamino-($C_1$–$C_4$)alkyl radicals; ($C_1$–$C_4$)alkoxy($C_1$–$C_4$)alkyl radicals; mono($C_1$–$C_4$)alkylamino($C_1$–$C_4$)alkyl radicals; di($C_1$–$C_4$)alkylamino($C_1$–$C_4$)alkyl radicals; aminocarboxy($C_1$–$C_4$)alkyl radicals; acetyl($C_1$–$C_4$)alkylamino($C_1$–$C_4$)alkyl radicals; and aromatic rings which are optionally substituted with at least one radical chosen from halogen atoms, $C_1$–$C_4$ alkyl radicals, trifluoromethyl radicals, $C_1$–$C_4$ alkoxy radicals, amino radicals, mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$)alkylamino($C_1$–$C_4$)alkyl radicals, carboxyl radicals and sulphoxy radicals;

$R_3$ may optionally further be chosen from 5- and 6-membered unsaturated heterocycles;

$R_2$ and $R_4$, which may be identical or different, are each chosen from hydrogen atoms; halogen atoms, Z groups; $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, mono($C_1$–$C_4$)-alkylamino($C_1$–$C_4$) alkyl radicals, di($C_1$–$C_4$)alkyl-amino($C_1$–$C_4$)alkyl radicals, carboxyl radicals, cyano radicals, carboxy($C_1$–$C_4$)alkyl radicals, nitro radicals and 5- and 6-membered aromatic rings which are optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino-($C_1$–$C_4$)alkyl radicals, di($C_1$–$C_4$)alkylamino-($C_1$–$C_4$) alkyl radicals, carboxyl radicals and sulphoxy radicals;

Z is chosen from the following unsaturated cationic groups of formulae (II) and (III) below, and the saturated cationic groups of formula (IV) below:

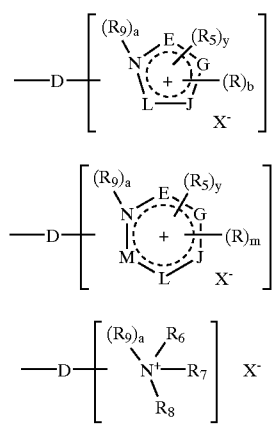

in which:
D is a linker arm which is chosen from linear and branched alkylene chains, preferably containing from 1 to 14 carbon atoms, which may be interrupted by at least one hetero atom, and which may be substituted with at least one substituent chosen from hydroxyl and $C_1$–$C_6$ alkoxy radicals, and which may bear at least one ketone function;

the ring members E, G, J, L and M, which may be identical or different, are chosen from carbon, oxygen, sulphur and nitrogen atoms;

b is an integer from 0 to 4;

m is an integer from 0 to 5;

the radicals R, which may be identical or different, are chosen from a second group Z, which may be identical to or different from the first group Z, halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$) alkyl radicals, $C_1$–$C_6$ alkoxy radicals, tri($C_1$–$C_6$) alkylsilane($C_1$–$C_6$)alkyl radicals, amido radicals, aldehydo radicals, carboxyl radicals, ($C_1$–$C_6$)alkylcarbonyl radicals, thio radicals, $C_1$–$C_6$ thioalkyl radicals, $C_1$–$C_6$ alkylthio radicals, amino radicals, amino radicals protected with at least one group chosen from ($C_1$–$C_6$) alkylcarbonyls, carbamyls and $C_1$–$C_6$ alkylsulphonyl radicals; NHR" and NR'R" groups in which R" and R"', which may be identical or different, are chosen from $C_1$–$C_6$ alkyl radicals, $C_1$–$C_6$ monohydroxyalkyl radicals and $C_2$–$C_6$ polyhydroxyalkyl radicals;

$R_5$ is chosen from $C_1$–$C_6$ alkyl radicals, $C_1$–$C_6$ monohydroxyalkyl radicals, $C_2$–$C_6$ polyhydroxyalkyl radicals, cyano($C_1$–$C_6$)alkyl radicals, tri($C_1$–$C_6$)-alkylsilane($C_1$–$C_6$)alkyl radicals, ($C_1$–$C_6$)alkoxy-($C_1$–$C_6$)alkyl radicals, carbamyl($C_1$–$C_6$)alkyl radicals, ($C_1$–$C_6$)alkylcarboxy($C_1$–$C_6$)alkyl radicals, benzyl radicals and second Z groups which may be identical to or different from the first Z groups;

$R_6$, $R_7$ and $R_8$, which may be identical or different, are each chosen from $C_1$–$C_6$ alkyl radicals, $C_1$–$C_6$ monohydroxyalkyl radicals, $C_2$–$C_6$ polyhydroxyalkyl radicals, ($C_1$–$C_6$)alkoxy($C_1$–$C_6$)alkyl radicals, cyano ($C_1$–$C_6$)alkyl radicals, aryl radicals, benzyl radicals, amido($C_1$–$C_6$)alkyl radicals, tri($C_1$–$C_6$)alkylsilane ($C_1$–$C_6$)alkyl radicals and $C_1$–$C_6$ aminoalkyl radicals in which the amine is protected with at least one group chosen from ($C_1$–$C_6$)alkylcarbonyls, carbamyls and $C_1$–$C_6$ alkylsulphonyl radicals; two of the radicals $R_6$, $R_7$ and $R_8$, may also form, together with the nitrogen atom to which they are attached, 5- and 6-membered saturated carbon-based rings and rings containing at least one hetero atom, such as, for example, a pyrrolidine ring, a piperidine ring, a piperazine ring or a morpholine ring, it being possible for the said ring to be optionally substituted with at least one substituent chosen from halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane($C_1$–$C_6$)alkyl radicals, amido radicals, aldehydo radicals, carboxyl radicals, keto($C_1$–$C_6$)alkyl radicals, thio radicals, $C_1$–$C_6$ thioalkyl radicals, $C_1$–$C_6$ alkylthio radicals, amino radicals and amino radical protected with at least one group chosen from ($C_1$–$C_6$)alkylcarbonyls, carbamyls and $C_1$–$C_6$ alkylsulphonyl radicals;

one of the radicals $R_6$, $R_7$ and $R_8$ may optionally be chosen from second Z groups, which may be identical to or different from the first Z groups;

$R_9$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is protected by at least one group chosen from ($C_1$–$C_6$) alkylcarbonyls, carbamyls and $C_1$–$C_6$ alkylsulphonyl radicals; carboxy($C_1$–$C_6$)alkyl radicals; cyano($C_1$–$C_6$) alkyl radicals; carbamyl($C_1$–$C_6$)alkyl radicals; $C_1$–$C_6$ trifluoroalkyl radicals; tri($C_1$–$C_6$)alkylsilane($C_1$–$C_6$) alkyl radicals; sulphonamido($C_1$–$C_6$)alkyl radicals; ($C_1$–$C_6$)alkylcarboxy($C_1$–$C_6$)alkyl radicals; ($C_1$–$C_6$) alkylsulphinyl($C_1$–$C_6$)alkyl radicals; ($C_1$–$C_6$) alkylsulphonyl($C_1$–$C_6$)alkyl radicals; ($C_1$–$C_6$) alkylketo($C_1$–$C_6$)alkyl radicals; N-($C_1$–$C_6$) alkylcarbamyl($C_1$–$C_6$)alkyl radicals; and N-($C_1$–$C_6$) alkylsulphonamido($C_1$–$C_6$)alkyl radicals;

a and y are integers equal to 0 or 1; with the following provisos:

in the unsaturated cationic groups of formula (II):
when a=0, the linker arm D is attached to the nitrogen atom,
when a=1, the linker arm D is attached to one of the ring members E, G, J and L,
y cannot take the value 1 except:
1) when the ring members E, G, J and L simultaneously represent a carbon atom, and when the radical $R_5$ is attached to the nitrogen atom of the unsaturated ring; or alternatively
2) when at least one of the ring members E, G, J and L represents a nitrogen atom to which the radical $R_5$ is attached;
when b is at least 2, two adjacent radicals R may also form together a ring chosen from unsaturated 5- and 6-membered carbon-based rings and rings containing at least one hetero atom;

in the unsaturated cationic groups of formula (III):
when a=0, the linker arm D is attached to the nitrogen atom,
when a=1, the linker arm D is attached to one of the ring members E, G, J, L and M,
y cannot take the value 1 except when at least one of the ring members E, G, J, L and M represents a divalent atom, and when the radical $R_5$ is attached to the nitrogen atom of the unsaturated ring;
when m is at least 2, two adjacent radicals R may also form together unsaturated 5- and 6-membered carbon-based rings and rings containing at least one hetero atom;

in the cationic groups of formula (IV):
when a=0, the linker arm D is attached to the nitrogen atom bearing the radicals $R_6$ to $R_8$,
when a=1, two of the radicals $R_6$ to $R_8$ form, together with the nitrogen atom to which they are attached, saturated 5- and 6-membered rings as defined above, and the linker arm D is attached to a carbon atom of the said saturated ring;

$X^-$ is chosen from monovalent and divalent anions and may be chosen, for example, from halides such as chloride, bromide, fluoride and iodide, hydroxides, hydrogen sulphates and $C_1$–$C_6$ alkyl sulphates such as, for example, methyl sulphates and ethyl sulphates;

it being understood that:
at least one of the radicals $R_1$ and $R_3$ represents a hydrogen atom; and
the number of cationic groups Z is at least equal to 1.

Colorations obtained using the inventive dye compositions may possess at least one of the following desirable characteristics: unselectivity, powerful, enable a variety of shades, and excellent properties of resistance to at least one of atmospheric agents chosen from light and bad weather, perspiration and treatments to which the hair may be subjected (such as shampooing, permanent-waving, etc.).

As used herein, "at least one" means one or more and thus includes individual components as well as mixtures/combinations. Further, as used herein, unless otherwise noted, alkyl radicals may be chosen from substituted, unsubstituted, linear, branched, and cyclic alkyl radicals. Similarly, as used herein and unless otherwise noted, the alkyl radicals of alkoxy radicals may be chosen from substituted, unsubstituted, linear, branched, and cyclic alkyl radicals.

Non-limiting examples of aromatic rings of formula (I) include phenyl rings, nitrophenyl rings, alkylphenyl rings, alkoxyphenyl rings, polyalkyl-phenylrings and polyalkoxyphenyl rings.

Non-limiting examples of unsaturated 5- and 6-membered heterocycles, such as may be represented by $R_3$, include pyrrole rings, pyridine rings, pyrimidine rings, imidazole rings, pyrazole rings, oxazole rings, thiazole rings, triazole rings, pyrazolotriazole rings, pyrazoloimidazole rings, pyrrolotriazole rings, pyrazolopyrimidine rings, pyrazolopyridine rings, benzimidazole rings, benzoxazole rings, benzothiazole rings, indole rings, indoline rings, indolidine rings, isoindolidine rings, benzotriazoline rings, pyrazine rings, oxazine rings, triazine rings, quinoline rings, tetrahydro-quinoline rings, benzimidazolidine rings and benzopyrimidine rings.

Non-limiting examples of unsaturated group Z rings of formula (II) include pyrrole rings, imidazole rings, pyrazole rings, oxazole rings, thiazole rings, triazole rings, pyrazoltriazolinium rings, pyrazoloimidazolinium rings, pyrrolotriazolinium rings, pyrazolopyrimidinium rings, pyrazolopyridinium rings, benzimidazolinium rings, benzoxazolinium rings, benzothiazolinium rings, indolinium rings, indolidinium rings, isoindolinium rings, indazolinium rings and benzotriazolinium rings.

Non-limiting examples of unsaturated group Z rings of formula (III) include pyridine rings, pyrimidine rings, pyrazine rings, oxazine rings, triazine rings, quinolinium rings and tetrahydroquinolinium rings.

Non-limiting examples of the compounds of formula (I) include:

N,N-dimethyl-2-phenyl-N-(phenylmethyl)-1-indolizinepropanaminium;

N,N,N-trimethyl-2-phenyl-1-indolizinethanaminium

N,N,N-trimethyl-2-phenyl-1-indolizinepropanaminium bromide;

4-methyl-4-[2-(2-phenyl-1-indolizinyl)ethyl]morpholinium bromide;

N,N-dimethyl-2-phenyl-N-(phenylmethyl)-1-indolizinepropanaminium nitrate;

N,N-dimethyl-2-phenyl-N-(phenylmethyl)-1-indolizinepropanaminium chloride;

N,N,N-trimethyl-2-phenyl-1-indolizinethanaminium methyl sulphate;

trimethyl[2-(2-phenyl-1-indolizinyl)ethyl]ammonium iodide;

trimethyl[2-(2-phenyl-1-indolizinyl)ethyl]ammonium bromide;

1-methyl-2-[2-(7-methyl-2-phenylindolizin-3-yl)ethyl] pyridinium methyl sulphate;

3-methyl-1-[2-(7-methyl-2-phenylindolizin-3-yl)-2-oxoethyl]-3H-imidazol-1-ium chloride;

3-methyl-1-[2-(2-methylindolizin-3-yl)-2-oxoethyl]-3H-imidazol-1-ium chloride;

1-{2-[2-(4-methoxyphenyl)-8-methylindolizin-3-yl]-2-oxoethyl}-3-methyl-3H-imidazol-1-ium chloride;

3-methyl-1-{2-[8-methyl-2-(3-nitrophenyl)indolizin-3-yl]-2-oxoethyl}-3H-imidazol-1-ium chloride;

1-{2-[2-(3-nitrophenyl)indolizin-3-yl]-2-oxoethyl}pyridinium chloride;

1-[2-oxo-2-(2-phenylindolizin-3-yl)ethyl]pyridinium chloride;

1-[2-oxo-2-(2-m-tolylindolizin-3-yl)ethyl]pyridinium chloride;

1-[2-(8,1-{2-[2-(4-methoxyphenyl)-8-methylindolizin-3-yl]-2-oxoethyl}-2-methylpyridinium chloride;

2-phenylindolizin-3-yl)-2-oxoethyl]pyridinium methyl chloride;

[2-(8-methyl-2-phenylindolizin-3-yl)-2-oxoethyl] pyridinium chloride;

2-methyl-1-{2-[2-(3-nitrophenyl)indolizin-3-yl]-2-oxoethyl}pyridinium chloride;

2-methyl-1-[2-oxo-2-(2-phenylindolizin-3-yl)ethyl] pyridinium chloride;

2-methyl-1-{2-[8-methyl-2-(3-nitrophenyl)indolizin-3-yl]-2-oxoethyl}pyridinium chloride;

2-methyl-1-[2-(8-methyl-2-phenylindolizin-3-yl )-2-oxoethyl]pyridinium chloride;

3-methoxycarbonyl-1-{2-[2-(3-nitrophenyl)indolizin-3-yl]-2-oxoethyl}pyridinium chloride;

3-methoxycarbonyl-1-[2-oxo-2-(2-phenylindolizin-3-yl)ethyl] pyridinium chloride;

3-methoxycarbonyl-1-{2-[2-(4-methoxyphenyl)-8-methylindolizin-3-yl]-2-oxoethyl}pyridinium chloride;

3-methoxycarbonyl-1-(2-[8-methyl-2-(3-nitrophenyl) indolizin-3-yl]-2-oxoethyl}pyridinium chloride;

3-methoxycarbonyl-1-[2-(8-methyl-2-phenylindolizin-3-yl)-2-oxoethyl] pyridinium chloride; and the acid addition salts thereof.

According to the present invention, the at least one coupler may be present in the composition in an amount generally ranging from 0.0005% to 12% by weight relative to the total weight of the dye composition, such as from 0.005% to 6% by weight.

The nature of the at least one oxidation base used in the present invention may not be critical. In one embodiment, the at least one oxidation base is chosen from para-phenylenediamines, double bases, para-aminophenols, ortho-aminophenols, heterocyclic oxidation bases, and the acid addition salts of any of the foregoing.

Non-limiting examples of para-phenylenediamines which can be used as the at least one oxidation base include compounds of formula (V) and the acid addition salts thereof:

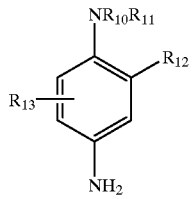

(V)

wherein:
- $R_{10}$ is chosen from a hydrogen atom, $C_1-C_4$ alkyl radicals, $C_1-C_4$ monohydroxyalkyl radicals, $C_2-C_4$ polyhydroxyalkyl radicals, $(C_1-C_4)$alkoxy$(C_1-C_4)$ alkyl radicals, $C_1-C_4$ alkyl radicals substituted with at least one radical chosen from nitrogen-containing radicals, phenyl radicals and 4'-aminophenyl radicals;
- $R_{11}$ is chosen from a hydrogen atom, $C_1-C_4$ alkyl radicals, $C_1-C_4$ monohydroxyalkyl radicals, $C_2-C_4$ polyhydroxyalkyl radicals, $(C_1-C_4)$alkoxy$(C_1-C_4)$ alkyl radicals and $C_1-C_4$ alkyl radicals substituted with at least one nitrogen-containing radical;
- $R_{12}$ is chosen from a hydrogen atom, halogen atoms such as a chlorine atom, a bromine atom, an iodine atom and a fluorine atom, $C_1-C_4$ alkyl radicals, $C_1-C_4$ monohydroxyalkyl radicals, $C_1-C_4$ hydroxyalkoxy radicals, acetylamino$(C_1-C_4)$alkoxy radicals, mesylamino-$(C_1-C_4)$alkoxy radicals and carbamoylamino$(C_1-C_4)$ alkoxy radicals;
- $R_{13}$ is chosen from a hydrogen atom, halogen atoms and $C_1-C_4$ alkyl radicals.

Non-limiting examples of nitrogen containing radicals of formula (V) above include amino radicals, mono$(C_1-C_4)$ alkylamino radicals, di$(C_1-C_4)$alkylamino radicals, tri $(C_1-C_4)$alkylamino radicals, monohydroxy$(C_1-C_4)$ alkylamino radicals, imidazolinium radicals and ammonium radicals.

Non-limiting examples of the para-phenylenediamines of formula (V) above include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(-hydroxyethyl)-para-phenylenediamine, 4-N,N-bis(-hydroxyethyl)amino-2-methylaniline, 4-N,N-bis(-hydroxyethyl)amino-2-chloroaniline, 2-hydroxyethyl-para-phenylenediamine, 2-fluoro-para-phenylenediamine, 2-isopropyl-para-phenylenediamine, N-(-hydroxypropyl)-para-phenylenediamine, 2-hydroxymethyl-para-phenylenediamine, N,N-dimethyl-3-methyl-para-phenylenediamine, N-ethyl-N-(-hydroxyethyl)-para-phenylenediamine, N-(,-dihydroxy-propyl)-para-phenylenediamine, N-(4'-aminophenyl)-para-phenylenediamine, N-phenyl-para-phenylenediamine, 2-hydroxyethyloxy-para-phenylenediamine, 2-acetylaminoethyloxy-para-phenylenediamine and N-(-methoxyethyl)-para-phenylenediamine, and acid addition salts of any of the foregoing.

In one embodiment, para-phenylenediamines of formula (V) above are chosen from para-phenylenediamine, para-tolylenediamine, 2-isopropyl-para-phenylenediamine, 2-hydroxyethyl-para-phenylenediamine, 2-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(-hydroxyethyl)-para-phenylenediamine, 2-chloro-para-phenylenediamine and 2-acetylaminoethyloxy-para-phenylenediamine, and the acid addition salts of any of the foregoing.

As used herein, "double bases" means compounds comprising at least two aromatic entities substituted with at least one radical chosen from amino radicals and hydroxyl radicals.

Non-limiting examples of double bases which may be used as the at least one oxidation base according to the present invention include compounds of formula (VI) and the acid addition salts thereof:

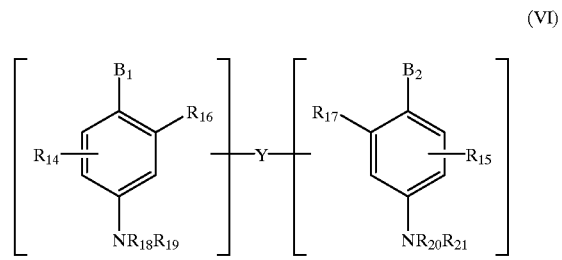

(VI)

in which:
- $B_1$ and $B_2$, which may be identical or different, are each chosen from hydroxyl radicals and $-NH_2$ radicals, optionally substituted with at least one radical chosen from $C_1-C_4$ alkyl radicals and linker arms Y;
- linker arm Y is chosen from linear and branched divalent alkylene chains comprising from 1 to 14 carbon atoms, wherein said divalent alkylene chains may optionally be interrupted by at least one nitrogen-containing radical and optionally interrupted by at least one hetero atom such as an oxygen atom, a sulphur atom or a nitrogen atom, further wherein said divalent alkylene chains may optionally be terminated with at least one nitrogen-containing radical and optionally interrupted by at least one heteroatom such as an oxygen atom, a sulphur atom or a nitrogen atom, and further wherein said divalent alkylene chains may optionally be substituted with at least one radical chosen from hydroxyl radicals and $C_1-C_6$ alkoxy radicals;
- $R_{14}$ and $R_{15}$, which may be identical or different, are each chosen from a hydrogen atom, halogen atoms, $C_1-C_4$ alkyl radicals, $C_1-C_4$ monohydroxyalkyl radicals, $C_2-C_4$ polyhydroxyalkyl radicals, $C_1-C_4$ aminoalkyl radicals and linker arms Y;
- $R_{16}$, $R_{17}$, $R_{18}$, $R_{19}$, $R_{20}$ and $R_{21}$, which may be identical or different, are each chosen from a hydrogen atom, linker arms Y and $C_1-C_4$ alkyl radicals;

with the proviso that only one linker arm Y is present in each compound of formula (III).

Non-limiting examples of double bases of formula (VI) include N,N'-bis($\beta$-hydroxyethyl)-N,N'-bis(4'-aminophenyl)-1,3-diaminopropanol, N,N'-bis($\beta$-hydroxyethyl)-N,N'-bis(4'-aminophenyl)ethylenediamine, N,N'-bis(4-aminophenyl)tetramethylenediamine, N,N'-bis ($\beta$-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4'-amino- 3'-methyl-phenyl)ethylenediamine, 1,8-bis(2,5-diaminophenoxy)-3,5-dioxaoctane, and the acid addition salts of any of the foregoing.

In one embodiment, double bases of formula (VI) are chosen from N,N'-bis(β-hydroxyethyl)-N,N'-bis(4'-aminophenyl)-1,3-diaminopropanol, 1,8-bis(2,5-diaminophenoxy)-3,5-dioxaoctane and the acid addition salts of any of the foregoing.

Non-limiting examples of para-aminophenols which may be used according to the present invention include compounds of formula (VII) and the acid addition salts thereof:

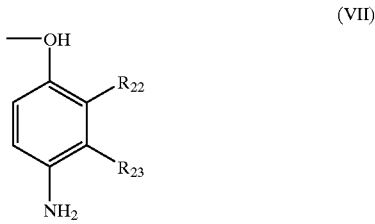

(VII)

wherein:
$R_{22}$ is chosen from a hydrogen atom, halogen atoms, $C_1$–$C_4$ alkyl radicals, $C_1$–$C_4$ monohydroxyalkyl radicals, ($C_1$–$C_4$)alkoxy($C_1$–$C_4$)alkyl radicals, $C_1$–$C_4$ aminoalkyl radicals and hydroxy($C_1$–$C_4$)alkylamino ($C_1$–$C_4$)alkyl radicals; and $R_{23}$ is chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, cyano($C_1$–$C_4$)alkyl radicals and ($C_1$–$C_4$)alkoxy($C_1$–$C_4$)alkyl radicals, with the proviso that at least one of $R_{22}$ and $R_{23}$ is a hydrogen atom.

Non-limiting examples of para-aminophenols of formula (VII) include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol and the acid addition salts of any of the foregoing.

Non-limiting examples of ortho-aminophenols which may be used as the at least one oxidation base include 2-aminophenol, 2-amino-5-methylphenol, 2-amino-6-methylphenol, 5-acetamido-2-aminophenol and the acid addition salts of any of the foregoing.

Non-limiting examples of heterocyclic bases which may be used as the at least one oxidation base include pyridine derivatives, pyrimidine derivatives, pyrazole derivatives and the acid addition salts of any of the foregoing.

Non-limiting examples of pyridine derivatives include compounds disclosed, for example, in British Patents GB 1 026 978 and GB 1 153 196, the disclosures of which are incorporated herein by reference, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine and the acid addition salts of any of the foregoing.

Non-limiting examples of pyrimidine derivatives include compounds described, for example, in German Patent DE 2 359 399, Japanese Patents JP 88-169 571 and JP 91-10659, and Patent Application WO 96/15765, the disclosures of which are incorporated herein by reference, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in patent application FR-A-2 750 048, the disclosure of which is incorporated herein by reference, such as pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, and the addition salts, tautomeric forms, (when a tautomeric equilibrium exists) and acid addition salts of any of the foregoing.

Further non-limiting examples of pyrazole derivatives include compounds described in German Patents DE 3 843 892 and DE 4 133 957 and Patent Applications WO 94/08969, WO 94/08970, FR-A-2 733 749 and DE 195 43 988, the disclosures of which are incorporated hereby by reference, such as 4,5-diamino-1-methylpyrazole, 3,4-diaminopyrazole, 4,5-diamino-1-(4'-chlorobenzyl)pyrazole, 4,5-diamino-1-(β-hydroxy-ethyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylamino-pyrazole, 3,5-diamino-4-(β-hydroxyethyl)amino-1-methylpyrazole, and the acid addition salts of any of the foregoing.

According to the present invention, the at least one oxidation base may be present in the composition in an amount generally ranging from 0.0005% to 12% by weight relative to the total weight of the dye composition, such as from 0.005% to 6% by weight.

The dye composition according to the present invention may optionally further comprise at least one additional coupler different from the indolizine derivatives of formula (I) and may optionally further comprise at least one direct dye, for example, to vary and/or enrich the shade obtained using the at least one oxidation base with highlights.

The at least one additional coupler which can be used in the dye composition according to with the present invention may be chosen from couplers, such as, for example, meta-phenylenediamines, meta-aminophenols, meta-diphenols and heterocyclic couplers such as, for example, indole derivatives, indoline derivatives, benzimidazole derivatives, benzomorpholine derivatives, sesamol derivatives, pyridine derivatives, pyrimidine derivatives, pyrazole derivatives and the acid addition salts thereof.

In one embodiment, the at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one and the addition salts of any of the foregoing.

When present, the at least one additional coupler may be present in the composition in an amount generally ranging 0.0001% to 10% by weight relative to the total weight of the dye composition, such as from 0.005% to 5% by weight.

According to the present invention, the acid addition salts may be chosen from hydrochlorides, hydrobromides, sulphates, tartrates, lactates and acetates.

The medium suitable for oxidation dyeing, or support, according to the present invention may be chosen from water and a mixture of water and at least one organic solvent in order to dissolve the compounds which might not be sufficiently soluble in water alone. Non-limiting examples of the at least one organic solvent includes $C_1$–$C_4$ alkanols such as ethanol and isopropanol; glycerol; glycols and glycol ethers such as 2-butoxyethanol, propylene glycol, propylene glycol monomethyl ether, diethylene glycol, diethylene glycol monomethyl ether; aromatic alcohols such as benzyl alcohol and phenoxyethanol; and analogous solvents.

According to the present invention, the at least one organic solvent maybe present in the composition in an amount generally ranging from 1% to 40% by weight relative to the total weight of the dye composition, such as from 5% to 30% by weight.

The pH of the dye composition in accordance with the present invention generally ranges from 3 to 12. It can be adjusted to the desired value by means of at least one agent commonly used in dyeing keratin fibres chosen from acidifying agents and basifying agents.

Non-limiting examples of acidifying agents include inorganic acids and organic acids such as hydrochloric acid, orthophosphoric acid, carboxylic acids (such as tartaric acid, citric acid and lactic acid) and sulphonic acids.

Non-limiting examples of basifying agents include aqueous ammonia, alkaline carbonates, alkanolamines such as mono-, di- and triethanolamines and derivatives thereof, sodium hydroxide, potassium hydroxide and compounds of formula (VIII):

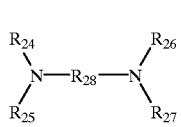

(VIII)

wherein:

$R_{28}$ is chosen from divalent propylene residues, optionally substituted with at least one radical chosen from hydroxyl radicals and $C_1$–$C_4$ alkyl radicals; $R_{24}$, $R_{25}$, $R_{26}$ and $R_{27}$, which may be identical or different, are each chosen from a hydrogen atom, $C_1$–$C_4$ alkyl radicals and $C_1$–$C_4$ hydroxyalkyl radicals.

According to the present invention, the dye composition may further comprise at least one adjuvant chosen from adjuvants conventionally used in hair dyeing compositions, such as anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickeners, organic thickeners, antioxidants, penetration agents, sequestering agents, fragrances, buffers, dispersing agents, conditioners, such as, for example, silicones, film-forming agents, preserving agents and opacifiers.

Needless to say, a person skilled in the art will take care to choose any optional additional compound(s) such that the advantageous properties associated with the inventive dye compositions are not, or not substantially, adversely affected by the addition(s) envisaged.

According to the present invention, the dye composition may be provided in various forms, such as in the form of a liquid, a cream or a gel, or in any other form suitable for dyeing keratin fibres, such as human hair.

Another subject of the present invention is a process for oxidation dyeing of keratin fibres comprising applying to said keratin fibres for a sufficient time to obtain a desired color at least one dye composition comprising, in a medium suitable for dyeing, (i) at least one coupler chosen from indolizine derivatives of formula (I) and acid addition salts thereofp; and (ii) at least one oxidation base. In one embodiment, the keratin fibres are chosen from human keratin fibres. In another embodiment, the human keratin fibres are hair.

In another embodiment, the at least one dye composition is applied to the keratin fibres, and the desired color may be developed at a pH chosen from acidic, neutral or alkaline pH. Further, the at least one dye composition may further comprise at least one oxidizing agent which may be added to the at least one dye composition at the time of application, and/or which may be present in at least one oxidizing composition. In one embodiment, the at least one oxidizing composition may be applied simultaneously with said at least one dye composition, while in another embodiment, the at least one oxidizing composition may be applied to the keratin fibres sequentially with the at least one dye composition.

In a further embodiment, the at least one dye composition is mixed, at the time of use, with at least one oxidizing composition comprising, in a medium appropriate for dyeing, at least one oxidizing agent present in an amount sufficient to develop a desired coloration. The mixture obtained may subsequently be applied to the keratin fibres and may be left to stand for 3 to 50 minutes, such as for 5 to 30 minutes. In yet another embodiment, the fibres are rinsed, and may optionally be washed with a shampoo, rinsed again and dried.

According to the present invention, the at least one oxidizing agent may be chosen from oxidizing agents conventionally used for the oxidation dyeing of keratin fibres, such as hydrogen peroxide, urea peroxide, alkali metal bromates, persalts such as perborates and persulphates, peracids and enzymes such as peroxidases, laccases, tyrosinases and oxidoreductases (such as pyranose oxidases, glucose oxidases, glycerol oxidases, lactate oxidases, pyruvate oxidases and uricases).

The pH of the at least one oxidizing composition comprising the at least one oxidizing agent after mixing with the at least one dye composition may generally range from 3 to 12, such as from 5 and 11. Further, the pH may be adjusted to a desired value by means of at least one agent chosen from acidifying and basifying agents commonly in dyeing keratin fibres and as defined above.

The at least one oxidizing composition as defined above may also contain at least one adjuvant conventionally used in hair dyeing compositions and as defined above.

The composition which is applied to the keratin fibres may be in various forms, such as in the form of a liquid, a cream or a gel or any other form suitable for carrying out dyeing of keratin fibres, such as human hair.

The present invention also provides a multi-compartment device or kit or any other packaging system, comprising a first compartment containing a first composition comprising at least one dye composition as defined above and a second compartment containing a second composition comprising at least one oxidizing composition as defined above. These devices may be equipped with a means allowing the desired mixture to be deposited on the hair, such as the devices described in French Patent FR-2 586 913, the disclosure of which is incorporated herein.

Finally, this invention provides certain novel indolizine derivatives of formula (I). These novel indolizine derivatives, and the acid addition salts thereof, correspond to formula (I) as defined above, with the following additional conditions:

Z cannot be chosen from the cationic groups of formula (IV) as defined above;
providing that 4-methyl-4-[2-(2-phenyl-1-indolizinyl) ethyl]morpholinium bromide is excluded.

The excluded compounds are known in the pharmaceutical field, as seen in patents U.S. Pat. No. 3,717,644 and U.S. Pat. No. 3,642,807.

In one embodiment, these novel indolizine derivatives may be chosen from:
1-methyl-2-[2-(7-methyl-2-phenylindolizin-3-yl)ethyl] pyridinium methyl sulphate;
3-methyl-1-[2-(7-methyl-2-phenylindolizin-3-yl)-2-oxoethyl]-3H-imidazol-1-ium chloride;
3-methyl-1-[2-(2-methylindolizin-3-yl)-2-oxoethyl]-3H-imidazol-1-ium chloride;
1-{2-[2-(4-methoxyphenyl)-8-methylindolizin-3-yl]-2-oxoethyl}-3-methyl-3H-imidazol-1-ium chloride;
3-methyl-1-{2-[8-methyl-2-(3-nitrophenyl)indolizin-3-yl]-2-oxoethyl}-3 H-imidazol-1-ium chloride;
1-{2-[2-(3-nitrophenyl)indolizin-3-yl]-2-oxoethyl}pyridinium chloride;
1-[2-oxo-2-(2-phenylindolizin-3-yl)ethyl]pyridinium chloride;
1-[2-oxo-2-(2-m-tolylindolizin-3-yl)ethyl]pyridinium chloride;
1-[2-(8,1-{2-[2-(4-methoxyphenyl)-8-methylindolizin-3-yl]-2-oxoethyl}-2-methylpyridinium chloride;
2-phenylindolizin-3-yl )-2-oxoethyl]pyridinium methyl chloride;
[2-(8-methyl-2-phenylindolizin-3-yl)-2-oxoethyl] pyridinium chloride;
2-methyl-1-{2-[2-(3-nitrophenyl)indolizin-3-yl]-2-oxoethyl}pyridinium chloride;
2-methyl-1-[2-oxo-2-(2-phenylindolizin-3-yl)ethyl] pyridinium chloride;
2-methyl-1-{2-[8-methyl-2-(3-nitrophenyl)indolizin-3-yl]-2-oxoethyl}pyridinium chloride;
2-methyl-1-[2-(8-methyl-2-phenylindolizin-3-yl)-2-oxoethyl]pyridinium chloride;
3-methoxycarbonyl-1-{2-[2-(3-nitrophenyl)indolizin-3-yl]-2-oxoethyl}pyridinium chloride;
3-methoxycarbonyl-1-[2-oxo-2-(2-phenylindolizin-3-yl) ethyl]pyridinium chloride;
3-methoxycarbonyl-1-{2-[2-(4-methoxyphenyl)-8-methylindolizin-3-yl]-2-oxoethyl}pyridinium chloride;
3-methoxycarbonyl-1-{2-[8-methyl-2-(3-nitropheny) indolizin-3-yl]-2-oxoethyl}pyridinium chloride;
3-methoxycarbonyl-1-[2-(8-methyl-2-phenylindolizin-3-yl)-2-oxoethyl]pyridinium chloride;
and the acid addition salts of any of the foregoing. The addition salts with an acid of the above novel compounds are chosen from those defined above for the compounds of formula (I).

These specific compounds may be prepared according to the synthetic process of indolizines comprising the step of reacting compounds chosen from alkyl-2 pyridine and aralkyl-2 pyridine with a haloacetone thus producing a pyridinium salt (Chichibabin, *Ber.* 1927, 60, 1607; Borrows, Holland, Kenyon, *J. Chem. Soc.* 1946, 1069). By reacting the salt with a base such as sodium bicarbonate in aqueous medium, indolinine is produced by cyclisation. Other methods for producing the indolizine nucleus are disclosed in T. Uchida et K. Matsumoto, *Synthesis*, 1976, 209–236. These compounds are then quaternized according to known conventional quaternization methods.

The compounds thus obtained can be purified by known methods such as distillation and crystallisation.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

PREPARATION EXAMPLES

Preparation Example 1

Synthesis of 1-methyl-2-[2-(7-methyl-2-phenylindolizin-3-yl)ethyl]pyridinium Methyl Sulphate Starting with the 7-methyl-2-phenylindolizine obtained according to the synthetic method of Chichibabin (Chichibabin *Ber.* 1927, 60, 1607), a catalytic addition of vinylpyridine was performed according to the method described by Pentimalli and Bozzini *Ann. Chimica* 1966, 56, 752. The 7-methyl-2-phenyl-3-(2-pyrid-2-ylethyl)indolizine thus obtained was treated with 3 molar equivalents of dimethyl sulphate in refluxing ethyl acetate. After reaction for two hours, the precipitate formed was filtered off and recrystallized from isopropyl alcohol, and the 1-methyl-2-[2-(7-methyl-2-phenylindolizin-3-yl)ethyl]pyridinium methyl sulphate was obtained in the form of a beige-coloured solid melting at a temperature of 204° C. (Kofler).

The $^1$H NMR analysis (DMSO-$d_6$, 400 MHz) ($\delta$ ppm) was as follows: 2.28 (s, 3H); 3.33 (t, 2H); 3.37 (s, 3H); 3.56

(t, 2H); 3.91 (s, 3H); 6.35 (s, 1 H); 6.53 (dd, 1 H); 7.22 (m, 1 H); 7.26 (m, 1 H); 7.30 (m, 2H); 7.35 (m, 2H); 7.79 (dd, 1H); 7.84 (ddd, 1 H); 8.22 (d, 1 H); 8.30 (ddd, 1 H); 8.78 (dd, 1 H).

Preparation Example 2

Synthesis of 3-methyl-1-[2-(7-methyl-2-phenylindolizin-3-yl)-2-oxoethyl]-3H-imidazol-1-ium Chloride Starting with the 7-methyl-2-phenylindolizine obtained according to the synthetic method of Chichibabin (Chichibabin *Ber.* 1927, 60,1607), acylation with chloroacetyl chloride was performed under the following conditions:

2.8 g (0.025 mol) of chloroacetyl chloride were added to a solution of 5 g (0.024 mol) of 7-methyl-2-phenylindolizine and 2.4 g (0.024 mol) of triethylamine in 300 ml of 1,2-dichloroethane. The medium was refluxed for 2 h 30 min and then cooled to room temperature. The reaction medium was washed 3 times with 100 ml of water and once with 100 ml of saturated sodium chloride solution. The organic phase was dried over sodium sulphate, filtered and concentrated on a rotary evaporator. The oil obtained was used in the following step without further purification.

The oil obtained was dissolved in 110 ml of ethyl acetate and the mixture was brought to reflux. 10 g (0.122 mol) of N-methylimidazole were added and refluxing was continued for one hour. The medium was then cooled to room temperature and the precipitate was filtered off, washed with ethyl acetate and then recrystallized from isopropyl alcohol. A very pale grey light solid melting at 250° C. (Kofler) was obtained.

The $^1$H NMR analysis (DMSO-$d_6$, 400 MHz) ($\delta$ ppm) was as follows: 2.40 (s, 3H); 3.89 (s, 3H); 5.04 (s, 2H); 6.59 (s, 1H); 7.02 (dd, 1H); 7.48–7.64 (m, 7H); 7.72 (dd, 1H); 9.14 (dd, 1 H); 9.71 (d, 1 H).

Preparation Example 3

Synthesis of 3-methyl-1-[2-(2-methylindolizin-3-yl)-2-oxoethyl]-3H-imidazol-1-ium Chloride The 2-methylindolizine obtained according to the Chichibabin synthesis was treated with chloroacetyl chloride as described previously in Preparation Example 2 above. The green powder obtained was used in the following quaternization step without further purification.

7.9 g of this green powder (0.0383 mol) were dissolved in 150 ml of ethyl acetate. 9.6 g (0.116 mol) of N-methylimidazole were added and the medium was brought to reflux. After refluxing for 3 hours, a further 9.6 g (0.116 mol) of N-methylimidazole were added. Refluxing was continued for 1 hour and the reaction medium was cooled to room temperature. The solid which precipitated was filtered off, washed with ethyl acetate and then recrystallized from isopropyl alcohol. A beige-coloured solid melting at a temperature above 260° C. (Kofler) was obtained.

The $^1$H NMR analysis (DMSO-$d_6$, 400 MHz) ($\delta$ ppm) was as follows: 2.69 (s, 3H); 3.98 (s, 3H); 5.90 (s, 2H); 6.62 (s, 1 H); 7.03 (dd, 1 H); 7.76 (unresolved multiplet, 3H); 9.20 (d, 1 H); 9.79 (d, 1 H).

DYEING EXAMPLES

Examples 1 to 4 of Dyeing in Alkaline Medium

The dye compositions below, in accordance with the invention, were prepared:

| EXAMPLE | 1 | 2 | 3 | 4 |
|---|---|---|---|---|
| 1-Methyl-2-[2-(7-methyl-2-phenylindolizin-3-yl)-ethyl]pyridinium methyl sulphate (coupler of formula (I)) | $3 \times 10^{-3}$ mol | $3 \times 10^{-3}$ mol | — | — |
| 3-Methyl-1-[2[(7-methyl-2-phenylindolizin-3-yl)-2-oxoethyl]-3H-imidazol-1-ium chloride (coupler of formula (I)) | — | — | $3 \times 10^{-3}$ mol | $3 \times 10^{-3}$ mol |
| para-Tolylenediamine (oxidation base) | $3 \times 10^{-3}$ mol | — | $3 \times 10^{-3}$ mol | — |
| 3,7-Diaminopyrazolopyrimidine dihydrochloride (oxidation base) | — | $3 \times 10^{-3}$ mol | — | $3 \times 10^{-3}$ mol |
| Common dye support | (*) | (*) | (*) | (*) |
| Demineralized water qs | 100 g | 100 g | 100 g | 100 g |

(*) Common dye support:
Ethanol 18 g
Aqueous ammonia containing 20% NH$_3$ 10 g
Sodium metabisulphite 0.205 g
Sequestering agent qs At the time of use, the above dye compositions were mixed weight for weight with a 20-volumes hydrogen peroxide solution (6% by weight) of pH 3.

The mixture obtained had a pH of about 10, and was applied for 30 minutes to locks of natural grey hair containing 90% white hairs. The locks were then rinsed, washed with shampoo, rinsed again and then dried.

The hair was dyed in a shade given in the table below.

| EXAMPLE | SHADE OBTAINED |
|---|---|
| 1 | Very matt golden blond |
| 2 | Very ashen natural blond |
| 3 | Slightly ashen golden blond |
| 4 | Very ashen iridescent blond |

What is claimed is:

1. A composition for dyeing keratin fibres, wherein the composition comprises, in a medium which is suitable for dyeing:
   (i) at least one oxidation base; and
   (ii) at least one coupler chosen from indolizine derivatives of formula (I) and the acid addition salts thereof:

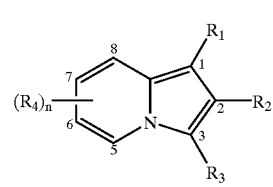

(I)

in which:
   n may be an integer from 0 to 4;
   $R_1$ and $R_3$, which may be identical or different, are each chosen from hydrogen atoms; halogen atoms; Z groups; $C_1$–$C_4$ alkyl radicals; $C_1$–$C_4$ alkoxy radicals; $C_1$–$C_4$ monohydroxyalkyl radicals; $C_2$–$C_4$ polyhydroxyalkyl radicals; $C_1$–$C_4$ aminoalkyl radicals; acetylamino radicals; acetylamino-($C_1$–$C_4$)alkyl radicals; ($C_1$–$C_4$)alkoxy($C_1$–$C_4$)alkyl radicals; mono($C_1$–$C_4$)

alkylamino($C_1$–$C_4$)alkyl radicals; di($C_1$–$C_4$)alkylamino($C_1$–$C_4$)alkyl radicals; aminocarboxy($C_1$–$C_4$)alkyl radicals; acetyl($C_1$–$C_4$)alkylamino($C_1$–$C_4$)alkyl radicals; and aromatic rings which are optionally substituted with at least one radical chosen from halogen atoms, $C_1$–$C_4$ alkyl radicals, trifluoromethyl radicals, $C_1$–$C_4$ alkoxy radicals, amino radicals, mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$)alkylamino($C_1$–$C_4$)alkyl radicals, carboxyl radicals and sulphoxy radicals;

$R_3$ may optionally further be chosen from 5- and 6-membered unsaturated heterocycles;

$R_2$ and $R_4$, which may be identical or different, are each chosen from hydrogen atoms; halogen atoms, Z groups; $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, mono($C_1$–$C_4$)-alkylamino($C_1$–$C_4$)alkyl radicals, di($C_1$–$C_4$)alkyl-amino($C_1$–$C_4$)alkyl radicals, carboxyl radicals, cyano radicals, carboxy($C_1$–$C_4$)alkyl radicals, nitro radicals and 5- and 6-membered aromatic rings which are optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino-($C_1$–$C_4$)alkyl radicals, di($C_1$–$C_4$)alkylamino-($C_1$–$C_4$)alkyl radicals, carboxyl radicals and sulphoxy radicals;

Z is chosen from the following unsaturated cationic groups of formulae (II) and (III) below, and the saturated cationic groups of formula (IV) below:

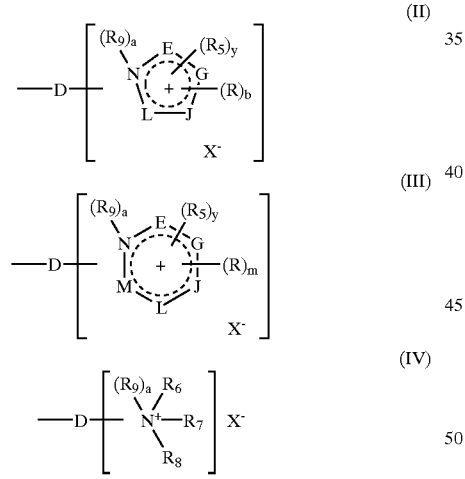

in which:
D is a linker arm which is chosen from linear and branched alkylene chains which may be interrupted by at least one hetero atom, and which may be substituted with at least one substituent chosen from hydroxyl and $C_1$–$C_6$ alkoxy radicals, and which may bear at least one ketone function;

the ring members E, G, J, L and M, which may be identical or different, are chosen from carbon, oxygen, sulphur and nitrogen atoms;

b is an integer from 0 to 4;

m is an integer from 0 to 5;

the radicals R, which may be identical or different, are chosen from a second group Z, which may be identical to or different from the first group Z, halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane($C_1$–$C_6$)alkyl radicals, amido radicals, aldehydo radicals, carboxyl radicals, ($C_1$–$C_6$)alkylcarbonyl radicals, thio radicals, $C_1$–$C_6$ thioalkyl radicals, $C_1$–$C_6$ alkylthio radicals, amino radicals, amino radicals protected with at least one group chosen from ($C_1$–$C_6$)alkylcarbonyls, carbamyls and $C_1$–$C_6$ alkylsulphonyl radicals; NHR" and NR"R'" groups in which R" and R'", which may be identical or different, are chosen from $C_1$–$C_6$ alkyl radicals, $C_1$–$C_6$ monohydroxyalkyl radicals and $C_2$–$C_6$ polyhydroxyalkyl radicals;

$R_5$ is chosen from $C_1$–$C_6$ alkyl radicals, $C_1$–$C_6$ monohydroxyalkyl radicals, $C_2$–$C_6$ polyhydroxyalkyl radicals, cyano($C_1$–$C_6$)alkyl radicals, tri($C_1$–$C_6$)-alkylsilane($C_1$–$C_6$)alkyl radicals, ($C_1$–$C_6$)alkoxy-($C_1$–$C_6$)alkyl radicals, carbamyl($C_1$–$C_6$)alkyl radicals, ($C_1$–$C_6$)alkylcarboxy($C_1$–$C_6$)alkyl radicals, benzyl radicals and second Z groups which may be identical to or different from the first Z groups;

$R_6$, $R_7$ and $R_8$, which may be identical or different, are each chosen from $C_1$–$C_6$ alkyl radicals, $C_1$–$C_6$ monohydroxyalkyl radicals, $C_2$–$C_6$ polyhydroxyalkyl radicals, ($C_1$–$C_6$)alkoxy($C_1$–$C_6$)alkyl radicals, cyano($C_1$–$C_6$)alkyl radicals, aryl radicals, benzyl radicals, amido($C_1$–$C_6$)alkyl radicals, tri($C_1$–$C_6$)alkylsilane($C_1$–$C_6$)alkyl radicals and $C_1$–$C_6$ aminoalkyl radicals in which the amine is protected with at least one group chosen from ($C_1$–$C_6$)alkylcarbonyls, carbamyls and $C_1$–$C_6$ alkylsulphonyl radicals; two of the radicals $R_6$, $R_7$ and $R_8$, may also form, together with the nitrogen atom to which they are attached, 5- and 6-membered saturated carbon-based rings and rings containing at least one hetero atom, it being possible for the said ring to be optionally substituted with at least one substituent chosen from halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane($C_1$–$C_6$)alkyl radicals, amido radicals, aldehydo radicals, carboxyl radicals, keto($C_1$–$C_6$)alkyl radicals, thio radicals, $C_1$–$C_6$ thioalkyl radicals, $C_1$–$C_6$ alkylthio radicals, amino radicals and amino radical protected with at least one group chosen from ($C_1$–$C_6$)alkylcarbonyls, carbamyls and $C_1$–$C_6$ alkylsulphonyl radicals;

one of the radicals $R_6$, $R_7$ and $R_8$ may optionally be chosen from second Z groups, which may be identical to or different from the first Z groups;

$R_9$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is protected by at least one group chosen from ($C_1$–$C_6$) alkylcarbonyls, carbamyls and $C_1$–$C_6$ alkylsulphonyl radicals; carboxy($C_1$–$C_6$)alkyl radicals; cyano($C_1$–$C_6$) alkyl radicals; carbamyl($C_1$–$C_6$)alkyl radicals; $C_1$–$C_6$ trifluoroalkyl radicals; tri($C_1$–$C_6$)alkylsilane($C_1$–$C_6$) alkyl radicals; sulphonamido($C_1$–$C_6$)alkyl radicals; ($C_1$–$C_6$)alkylcarboxy($C_1$–$C_6$)alkyl radicals; ($C_1$–$C_6$) alkylsulphinyl($C_1$–$C_6$)alkyl radicals; ($C_1$–$C_6$) alkylsulphonyl($C_1$–$C_6$)alkyl radicals; ($C_1$–$C_6$) alkylketo($C_1$–$C_6$)alkyl radicals; N-($C_1$–$C_6$) alkylcarbamyl($C_1$–$C_6$)alkyl radicals; and N-($C_1$–$C_6$) alkylsulphonamido($C_1$–$C_6$)alkyl radicals;

a and y are integers equal to 0 or 1; with the following provisos:

in the unsaturated cationic groups of formula (II):
when a=0, the linker arm D is attached to the nitrogen atom,
when a=1, the linker arm D is attached to one of the ring members E, G, J and L,
y cannot take the value 1 except:
1) when the ring members E, G, J and L simultaneously represent a carbon atom, and when the radical $R_5$ is attached to the nitrogen atom of the unsaturated ring; or alternatively
2) when at least one of the ring members E, G, J and L represents a nitrogen atom to which the radical $R_5$ is attached;
when b is at least 2, two adjacent radicals R may also form together a ring chosen from unsaturated 5- and 6-membered carbon-based rings and rings containing at least one hetero atom;

in the unsaturated cationic groups of formula (III):
when a=0, the linker arm D is attached to the nitrogen atom,
when a=1, the linker arm D is attached to one of the ring members E, G, J, L and M,
y cannot take the value 1 except when at least one of the ring members E, G, J, L and M represents a divalent atom, and when the radical $R_5$ is attached to the nitrogen atom of the unsaturated ring;
when m is at least 2, two adjacent radicals R may also form together unsaturated 5- and 6-membered carbon-based rings and rings containing at least one hetero atom;

in the cationic groups of formula (IV):
when a=0, the linker arm D is attached to the nitrogen atom bearing the radicals $R_6$ to $R_8$,
when a=1, two of the radicals $R_6$ to $R_8$ form, together with the nitrogen atom to which they are attached, saturated 5- and 6-membered rings as defined above, and the linker arm D is attached to a carbon atom of the said saturated ring;

$X^-$ is chosen from monovalent and divalent anions; it being understood that:

at least one of the radicals $R_1$ and $R_3$ represents a hydrogen atom; and wherein at least one of R1, R2, R3 or R4 is a Z group.

2. The composition according to claim 1, wherein $R_3$ is an unsaturated heterocycle chosen from pyrrole rings, pyridine rings, pyrimidine rings, imidazole rings, pyrazole rings, oxazole rings, thiazole rings, triazole rings, pyrazolotriazole rings, pyrazoloimidazole rings, pyrrolotriazole rings, pyrazolopyrimidine rings, pyrazolopyridine rings, benzimidazole rings, benzoxazole rings, benzothiazole rings, indole rings, indoline rings, indolidine rings, isoindolidine rings, benzotriazoline rings, pyrazine rings, oxazine rings, triazine rings, quinoline rings, tetrahydroquinoline rings, benzimidazolidine rings and benzopyrimidine rings.

3. The composition according to claim 1, wherein the rings in the unsaturated Z groups of formula (II) are chosen from pyrrole rings, imidazole rings, pyrazole rings, oxazole rings, thiazole rings, triazole rings, pyrazoltriazolinium rings, pyrazoloimidazolinium rings, pyrrolotriazolinium rings, pyrazolopyrimidinium rings, pyrazolopyridinium rings, benzimidazolinium rings, benzoxazolinium rings, benzothiazolinium rings, indolinium rings, indolidinium rings, isoindolinium rings, indazolinium rings and benzotriazolinium rings.

4. The composition according to claim 1, wherein the rings in the unsaturated Z groups of formula (III) are chosen from pyridine rings, pyrimidine rings, pyrazine rings, oxazine rings, triazine rings, quinolinium rings, tetrahydroquinolinium rings, benzimidazolidinium rings and benzopyrimidinium rings.

5. The composition according to claim 1, wherein X- is chosen from halides, hydroxides, hydrogen sulphates and $(C_1-C_6)$alkyl sulphates.

6. The composition according to claim 1, (wherein the indolizine derivatives of formula (I) are chosen from:

N,N-dimethyl-2-phenyl-N-(phenylmethyl)-1-indolizinepropanaminium;

N,N,N-trimethyl-2-phenyl-1-indolizinethanaminium

N,N,N-trimethyl-2-phenyl-1-indolizinepropanaminium bromide;

4-methyl-4-[2-(2-phenyl-1-indolizinyl )ethyl] morpholinium bromide;

N,N-dimethyl-2-phenyl-N-(phenylmethyl)-1-indolizinepropanaminium nitrate;

N,N-dimethyl-2-phenyl-N-(phenylmethyl)-1-indolizinepropanaminium chloride;

N,N,N-trimethyl-2-phenyl-1-indolizinethanaminium methyl sulphate;

trimethyl[2-(2-phenyl-1-indolizinyl)ethyl]ammonium iodide;

trimethyl[2-(2-phenyl-1 -indolizinyl)ethyl]ammonium bromide;

1-methyl-2-[2-(7-methyl-2-phenylindolizin-3-yl)ethyl] pyridinium methyl sulphate;

3-methyl-1-[2-(7-methyl-2-phenylindolizin-3-yl)-2-oxoethyl]-3H-imidazol-1-ium chloride;

3-methyl-1-[2-(2-methylindolizin-3-yl)-2-oxoethyl]-3H-imidazol-1-ium chloride;

1-{2-[2-(4-methoxyphenyl)-8-methylindolizin-3-yl]-2-oxoethyl}-3-methyl-3H-imidazol-1-ium chloride;

3-methyl-1-{2-[8-methyl-2-(3-nitrophenyl)indolizin-3-yl]-2-oxoethyl}-3 H-imidazol-1-ium chloride;

1-{2-[2-(3-nitrophenyl)indolizin-3-yl]-2-oxoethyl}pyridinium chloride;

1-[2-oxo-2-(2-phenylindolizin-3-yl)ethyl]pyridinium chloride;

1-[2-oxo-2-(2-m-tolylindolizin-3-yl)ethyl]pyridinium chloride;

1-[2-(8,1-{2-[2-(4-methoxyphenyl)-8-methylindolizin-3-yl]-2-oxoethyl}-2-methylpyridinium chloride;

2-phenylindolizin-3-yl )-2-oxoethyl]pyridinium methyl chloride;

[2-(8-methyl-2-phenylindolizin-3-yl)-2-oxoethyl] pyridinium chloride;

2-methyl-1-{2-[2-(3-nitrophenyl)indolizin-3-yl]-2-oxoethyl}pyridinium chloride;

2-methyl-1-[2-oxo-2-(2-phenylindolizin-3-yl)ethyl] pyridinium chloride;

2-methyl-1-{2-[8-methyl-2-(3-nitrophenyl)indolizin-3-yl]-2-oxoethyl}pyridinium chloride;

2-methyl-1-[2-(8-methyl-2-phenylindolizin-3-yl)-2-oxoethyl]pyridinium chloride;

3-methoxycarbonyl-1-{2-[2-(3-nitropheny)indolizin-3-yl]-2-oxoethyl}pyridinium chloride;

3-methoxycarbonyl-1-[2-oxo-2-(2-phenylindolizin-3-yl )ethyl]pyridinium chloride;

3-methoxycarbonyl-1-{2-[2-(4-methoxyphenyl )-8-methylindolizin-3-yl]-2-oxoethyl}pyridinium chloride;

3-methoxycarbonyl-1-{2-[2-(3-nitrophenyl)indolizin-3-yl]-2-oxoethyl}pyridinium chloride;

3-methoxycarbonyl-1-[2-(8-methyl-2-phenylindolizin-3-yl)-2-oxoethyl]pyridinium chloride;

and the addition salts thereof with an acid.

7. The composition according to claim 1, wherein said at least one coupler is present in an amount ranging from 0.0005% to 12% by weight relative to the total weight of said composition.

8. The composition according to claim 7, wherein said at least one coupler is present in an amount ranging from 0.005% to 6% by weight relative to the total weight of said composition.

9. The composition according to claim 1, wherein said at least one oxidation base is chosen from para-phenylenediamines, double bases, para-aminophenols, ortho-aminophenols and heterocyclic oxidation bases, and the acid addition salts of the foregoing.

10. The composition according to claim 9, wherein the para-phenylenediamines are chosen from the compounds of formula (V) below, and the addition salts thereof with an acid:

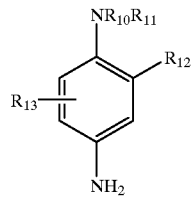

(V)

in which:

$R_{10}$ is chosen from a hydrogen atom, $C_1$–$C_4$ alkyl radicals, $C_1$–$C_4$ monohydroxyalkyl radicals, $C_2$–$C_4$ polyhydroxyalkyl radicals, $(C_1$–$C_4)$alkoxy$(C_1$–$C_4)$ alkyl radicals, $C_1$–$C_4$ alkyl radicals substituted with at least one radical chosen from nitrogen-containing radicals, phenyl radicals and 4'-aminophenyl radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals, $(C_1$–$C_4)$alkoxy$(C_1$–$C_4)$ alkyl radicals and $C_1$–$C_4$ alkyl radicals substituted with at least one nitrogen-containing radical;

$R_{12}$ is chosen from a hydrogen atom, halogen atoms, $C_1$–$C_4$ alkyl radicals, $C_1$–$C_4$ monohydroxyalkyl radicals, $C_1$–$C_4$ hydroxyalkoxy radicals, acetylamino $(C_1$–$C_4)$alkoxy radicals, mesylamino$(C_1$–$C_4)$alkoxy radicals and carbamoylamino$(C_1$–$C_4)$alkoxy radicals;

$R_{13}$ is chosen from a hydrogen atom, halogen atoms and $C_1$–$C_4$ alkyl radicals.

11. The composition according to claim 10, wherein said halides are chosen from chloride, bromides iodide, and fluoride.

12. The composition according to claim 10, wherein said nitrogen-containing radicals are chosen from amino radicals, mono$(C_1$–$C_4)$alkylamino radicals, di$(C_1$–$C_4)$alkylamino radicals, tri$(C_1$–$C_4)$alkylamino radicals, monohydroxy $(C_1$–$C_4)$alkylamino radicals, imidazolinium radicals and ammonium radicals.

13. The composition according to claim 9, wherein the para-phenylenediamines are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(-hydroxyethyl)-para-phenylenediamine, 4-N,N-bis(-hydroxyethyl)amino-2-methylaniline, 4-N,N-bis(-hydroxyethyl)amino-2-chloroaniline, 2-hydroxyethyl-para-phenylenediamine, 2-fluoro-para-phenylenediamine, 2-isopropyl-para-phenylenediamine, N-(-hydroxypropyl)-para-phenylenediamine, 2-hydroxymethyl-para-phenylenediamine, N,N-dimethyl-3-methyl-para-phenylenediamine, N-ethyl-N-(-hydroxyethyl)-para-phenylenediamine, N-(-dihydroxypropyl)-para-phenylenediamine, N-(4'-aminophenyl)-para-phenylenediamine, N-phenyl-para-phenylenediamine, 2-hydroxyethyloxy-para-phenylenediamine, 2-acetylaminoethyloxy-para-phenylenediamine and N-(-methoxyethyl)-para-phenylenediamine, and the addition salts thereof with an acid.

14. The composition according to claim 13, wherein said para-phenylenediamines are chosen from para-phenylenediamine, para-tolylenediamine, 2-iso-propyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts of any of the foregoing.

15. The composition according to claim 9, wherein the double bases are chosen from the compounds corresponding to formula (VI) below, and the acid addition salts thereof:

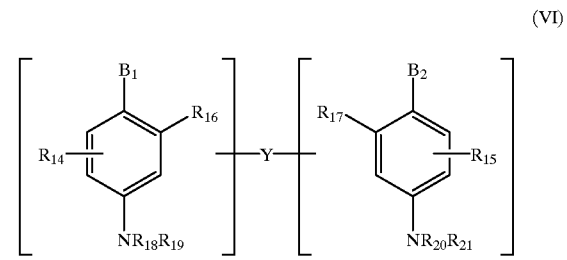

(VI)

wherein:

$B_1$ and $B_2$, which may be identical or different, are each chosen from hydroxyl radicals and —$NH_2$ radicals, optionally substituted with at least one radical chosen from $C_1$–$C_4$ alkyl radicals and linker arms Y;

linker arm Y is chosen from linear and branched divalent alkylene chains comprising from 1 to 14 carbon atoms, wherein said divalent alkylene chains may optionally be interrupted by at least one nitrogen-containing radical and optionally interrupted by at least one hetero atom such as an oxygen atom, a sulphur atom or a nitrogen atom, further wherein said divalent alkylene chains may optionally be terminated with at least one nitrogen-containing radical and optionally interrupted by at least one heteroatom such as an oxygen atom, a sulphur atom or a nitrogen atom, and further wherein said divalent alkylene chains may optionally be substituted with at least one radical chosen from hydroxyl radicals and $C_1$–$C_6$ alkoxy radicals;

$R_{14}$ and $R_{15}$, which may be identical or different, are each chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals and linker arms Y;

$R_{16}$, $R_{17}$, $R_{18}$, $R_{19}$, $R_{20}$ and $R_{21}$, which may be identical or different, are each chosen from a hydrogen atom, linker arms Y and $C_1$–$C_4$ alkyl radicals; with the proviso that only one linker arm Y is present in each compound of formula (VI).

16. The composition according to claim 15, wherein the double bases of formula (VI) are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(p-hydroxyethyl)-N,N'-bis (4-aminophenyl)tetramethylenediamine, N,N'-bis(4-methylaminophenyl )tetramethylenediamine, N,N'-bis (ethyl)-N,N'-bis(4'-amino-3'-methylphenyl) ethylenediamine, 1,8-bis(2,5-diaminophenoxy)-3,5-dioxaoctane, and the acid addition salts of any of the foregoing.

17. A composition according to claim 16, wherein said double bases are chosen from N,N'-bis(β-hydroxyethyl)-N, N'-bis(4'-aminophenyl)-1,3-diaminopropanol, 1,8-bis(2,5-diaminophenoxy)-3,5-dioxaoctane and the acid addition salts of any of the foregoing.

18. The composition according to claim 9, wherein the para-aminophenols are chosen from the compounds corresponding to formula (VII) below, and the acid addition salts thereof:

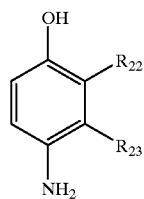

(VII)

wherein:
$R_{22}$ is chosen from a hydrogen atom, halogen atoms, $C_1$–$C_4$ alkyl radicals, $C_1$–$C_4$ monohydroxyalkyl radicals, ($C_1$–$C_4$)alkoxy($C_1$–$C_4$)alkyl radicals, $C_1$–$C_4$ aminoalkyl radicals and hydroxy($C_1$–$C_4$)alkylamino ($C_1$–$C_4$)alkyl radicals; and $R_{23}$ is chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, cyano($C_1$–$C_4$)alkyl radicals and ($C_1$–$C_4$)alkoxy($C_1$–$C_4$)alkyl radicals, with the proviso that at least one of $R_{22}$ and $R_{23}$ is a hydrogen atom.

19. The composition according to claim 18, wherein the para-aminophenols are chosen from para-aminophenol, 4-amino-3-methylphenol, 4-amino-3-fluorophenol, 4-amino-3-hydroxymethylphenol, 4-amino-2-methyl phenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts of any of the foregoing.

20. A composition according to claim 9, wherein said ortho-aminophenols are chosen from 2-aminophenol, 2-amino-5-methylphenol, 2-amino-6-methylphenol, 5-acetamido-2-aminophenol and the acid addition salts of any of the foregoing.

21. The composition according to claim 1, wherein the at least one oxidation base is present in an amount generally ranging from 0.0005% to 12% by weight relative to the total weight of the dye composition.

22. The composition according to claim 1, wherein said composition contains at least one additional coupler and at least one direct dye.

23. The composition according to claim 22, wherein the at least one additional coupler is chosen from meta-phenylenediamines, meta-aminophenols, meta-diphenols and heterocyclic couplers.

24. The composition according to claim 22, wherein the at least one additional coupler is present in an amount generally ranging from 0.0001% to 10% relative to the total weight of the dye composition.

25. The composition according to claim 1, wherein the acid addition salts are chosen from the hydrochlorides, hydrobromides, sulphates, tartrates, lactates and acetates.

26. The composition according to claim 1, wherein said composition is in the form of a liquid, a cream or a gel.

27. The composition according to claim 1, wherein said linker arm D is chosen from linear and branched alkylene chains containing from 1 to 14 carbon atoms.

28. A process for oxidation dyeing of keratin fibres comprising:
applying to said keratin fibres for a sufficient time to develop a desired color at least one dye composition comprising, in a medium suitable for dyeing, (i) at least one oxidation base and (ii) at least one coupler chosen from indolizine derivatives of formula (I) and the acid addition salts thereof:

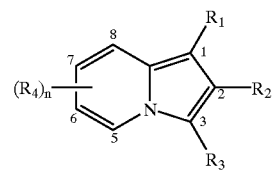

(I)

wherein:
n may be an integer from 0 to 4;

$R_1$ and $R_3$, which may be identical or different, are each chosen from hydrogen atoms; halogen atoms; Z groups; $C_1$–$C_4$ alkyl radicals; $C_1$–$C_4$ alkoxy radicals; $C_1$–$C_4$ monohydroxyalkyl radicals; $C_2$–$C_4$ polyhydroxyalkyl radicals; $C_1$–$C_4$ aminoalkyl radicals; acetylamino radicals; acetylamino-($C_1$–$C_4$)alkyl radicals; ($C_1$–$C_4$)alkoxy($C_1$–$C_4$)alkyl radicals; mono($C_1$–$C_4$) alkylamino($C_1$–$C_4$)alkyl radicals; di($C_1$–$C_4$) alkylamino($C_1$–$C_4$)alkyl radicals; aminocarboxy ($C_1$–$C_4$)alkyl radicals; acetyl($C_1$–$C_4$)alkylamino ($C_1$–$C_4$)alkyl radicals; and aromatic rings which are optionally substituted with at least one radical chosen from halogen atoms, $C_1$–$C_4$ alkyl radicals, trifluoromethyl radicals, $C_1$–$C_4$ alkoxy radicals, amino radicals, mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$) alkylamino($C_1$–$C_4$)alkyl radicals, carboxyl radicals and sulphoxy radicals; $R_3$ may optionally further be chosen from 5- and 6-membered unsaturated heterocycles;

$R_2$ and $R_4$, which may be identical or different, are each chosen from hydrogen atoms; halogen atoms, Z groups; $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, mono($C_1$–$C_4$)-alkylamino($C_1$–$C_4$) alkyl radicals, di($C_1$–$C_4$)alkyl-amino($C_1$–$C_4$)alkyl radicals, carboxyl radicals, cyano radicals, carboxy($C_1$–$C_4$)alkyl radicals, nitro radicals and 5- and 6-membered aromatic rings which are optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino-($C_1$–$C_4$)alkyl radicals, di($C_1$–$C_4$)alkylamino-($C_1$–$C_4$) alkyl radicals, carboxyl radicals and sulphoxy radicals;

Z is chosen from the following unsaturated cationic groups of formulae (II) and (III) below, and the saturated cationic groups of formula (IV) below:

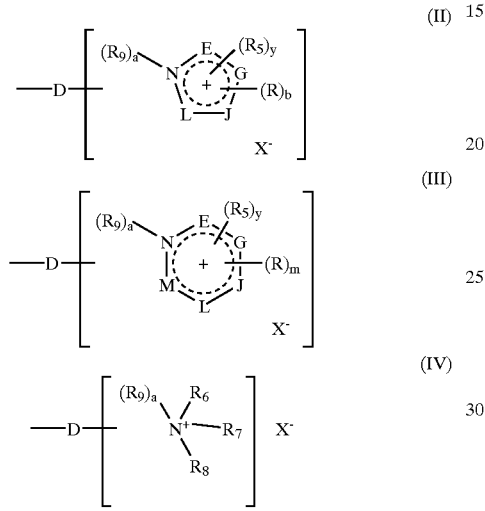

in which:

D is a linker arm which is chosen from linear and branched alkylene chains which may be interrupted by at least one hetero atom, and which may be substituted with at least one substituent chosen from hydroxyl and $C_1$–$C_6$ alkoxy radicals, and which may bear at least one ketone function;

the ring members E, G, J, L and M, which may be identical or different, are chosen from carbon, oxygen, sulphur and nitrogen atoms;

b is an integer from 0 to 4;

m is an integer from 0 to 5;

the radicals R, which may be identical or different, are chosen from a second group Z, which may be identical to or different from the first group Z, halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$) alkyl radicals, $C_1$–$C_6$ alkoxy radicals, tri($C_1$–$C_6$) alkylsilane($C_1$–$C_6$)alkyl radicals, amido radicals, aldehydo radicals, carboxyl radicals, ($C_1$–$C_6$)alkylcarbonyl radicals, thio radicals, $C_1$–$C_6$ thioalkyl radicals, $C_1$–$C_6$ alkylthio radicals, amino radicals, amino radicals protected with at least one group chosen from ($C_1$–$C_6$) alkylcarbonyls, carbamyls and $C_1$–$C_6$ alkylsulphonyl radicals; NHR' and NR"R'" groups in which R" and R'", which may be identical or different, are chosen from $C_1$–$C_6$ alkyl radicals, $C_1$–$C_6$ monohydroxyalkyl radicals and $C_2$–$C_6$ polyhydroxyalkyl radicals;

$R_5$ is chosen from $C_1$–$C_6$ alkyl radicals, $C_1$–$C_6$ monohydroxyalkyl radicals, $C_2$–$C_6$ polyhydroxyalkyl radicals, cyano($C_1$–$C_6$)alkyl radicals, tri($C_1$–$C_6$)-alkylsilane($C_1$–$C_6$)alkyl radicals, ($C_1$–$C_6$)alkoxy-($C_1$–$C_6$)alkyl radicals, carbamyl($C_1$–$C_6$)alkyl radicals, ($C_1$–$C_6$)alkylcarboxy($C_1$–$C_6$)alkyl radicals, benzyl radicals and second Z groups which may be identical to or different from the first Z groups;

$R_6$, $R_7$ and $R_8$, which may be identical or different, are each chosen from $C_1$–$C_6$ alkyl radicals, $C_1$–$C_6$ monohydroxyalkyl radicals, $C_2$–$C_6$ polyhydroxyalkyl radicals, ($C_1$–$C_6$)alkoxy($C_1$–$C_6$)alkyl radicals, cyano ($C_1$–$C_6$)alkyl radicals, aryl radicals, benzyl radicals, amido($C_1$–$C_6$)alkyl radicals, tri($C_1$–$C_6$)alkylsilane ($C_1$–$C_6$)alkyl radicals and $C_1$–$C_6$ aminoalkyl radicals in which the amine is protected with at least one group chosen from ($C_1$–$C_6$)alkylcarbonyls, carbamyls and $C_1$–$C_6$ alkylsulphonyl radicals; two of the radicals $R_6$, $R_7$ and $R_8$, may also form, together with the nitrogen atom to which they are attached, 5- and 6-membered saturated carbon-based rings and rings containing at least one hetero atom, it being possible for the said ring to be optionally substituted with at least one substituent chosen from halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane($C_1$–$C_6$)alkyl radicals, amido radicals, aldehydo radicals, carboxyl radicals, keto($C_1$–$C_6$)alkyl radicals, thio radicals, $C_1$–$C_6$ thioalkyl radicals, $C_1$–$C_6$ alkylthio radicals, amino radicals and amino radical protected with at least one group chosen from ($C_1$–$C_6$)alkylcarbonyls, carbamyls and $C_1$–$C_6$ alkylsulphonyl radicals;

one of the radicals $R_6$, $R_7$ and $R_8$ may optionally be chosen from second Z groups, which may be identical to or different from the first Z groups;

$R_9$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is protected by at least one group chosen from ($C_1$–$C_6$) alkylcarbonyls, carbamyls and $C_1$–$C_6$ alkylsulphonyl radicals; carboxy($C_1$–$C_6$)alkyl radicals; cyano($C_1$–$C_6$) alkyl radicals; carbamyl($C_1$–$C_6$)alkyl radicals; $C_1$–$C_6$ trifluoroalkyl radicals; tri($C_1$–$C_6$)alkylsilane($C_1$–$C_6$) alkyl radicals; sulphonamido($C_1$–$C_6$)alkyl radicals; ($C_1$–$C_6$)alkylcarboxy($C_1$–$C_6$)alkyl radicals; ($C_1$–$C_6$) alkylsulphinyl($C_1$–$C_6$)alkyl radicals; ($C_1$–$C_6$) alkylsulphonyl($C_1$–$C_6$)alkyl radicals; ($C_1$–$C_6$) alkylketo($C_1$–$C_6$)alkyl radicals; N-($C_1$–$C_6$) alkylcarbamyl($C_1$–$C_6$)alkyl radicals; and N-($C_1$–$C_6$) alkylsulphonamido($C_1$–$C_6$)alkyl radicals;

a and y are integers equal to 0 or 1; with the following provisos:

in the unsaturated cationic groups of formula (II):
when a=0, the linker arm D is attached to the nitrogen atom,
when a=1, the linker arm D is attached to one of the ring members E, G, J and L,
y cannot take the value 1 except:
1) when the ring members E, G, J and L simultaneously represent a carbon atom, and when the radical $R_5$ is attached to the nitrogen atom of the unsaturated ring; or alternatively
2) when at least one of the ring members E, G, J and L represents a nitrogen atom to which the radical $R_5$ is attached;
when b is at least 2, two adjacent radicals R may also form together a ring chosen from unsaturated 5- and 6-membered carbon-based rings and rings containing at least one hetero atom;
in the unsaturated cationic groups of formula (III):
when a=0, the linker arm D is attached to the nitrogen atom,
when a=1, the linker arm D is attached to one of the ring members E, G, J, L and M,
y cannot take the value 1 except when at least one of the ring members E, G, J, L and M represents a divalent atom, and when the radical $R_5$ is attached to the nitrogen atom of the unsaturated ring;
when m is at least 2, two adjacent radicals R may also form together unsaturated 5- and 6-membered carbon-based rings and rings containing at least one hetero atom;
in the cationic groups of formula (IV):
when a=0, the linker arm D is attached to the nitrogen atom bearing the radicals $R_6$ to $R_8$,
when a =1, two of the radicals $R_6$ to $R_8$ form, together with the nitrogen atom to which they are attached, saturated 5- and 6-membered rings as defined above, and the linker arm D is attached to a carbon atom of the said saturated ring;

$X^-$ is chosen from monovalent and divalent anions;
it being understood that:
at least one of the radicals $R_1$ and $R_3$ represents a hydrogen atom; and
wherein at least one of R1, R2, R3 or R4 is a Z group.

29. The composition according to claim 28, wherein said linker arm D is chosen from linear and branched alkylene chains containing from 1 to 14 carbon atoms.

30. The process according to claim 28, wherein said keratin fibres are human hair.

31. A process according to claim 28, further comprising applying to said keratin fibres at least one oxidizing composition.

32. A process according to claim 28, wherein said at least one dye composition further comprises at least one oxidizing agent.

33. A process according to claim 28, wherein said desired color is developed at acidic, neutral or alkaline pH.

34. A process according to claim 32, wherein said at least one oxidizing agent is added to said at least one dye composition at the time of application.

35. A process according to claim 31, wherein said at least one oxidizing composition comprises at least one oxidizing agent.

36. A process according to claim 31, wherein said at least one oxidizing composition is applied to said keratin fibres simultaneously with said at least one dye composition.

37. A process according to claim 31, wherein said at least one oxidizing composition is applied to said keratin fibres sequentially with said at least one composition.

38. A process according to claim 31, wherein said at least one oxidizing composition is mixed with said at least one dye composition prior to said applying.

39. A process according to claim 28, wherein said keratin fibres are human keratin fibres.

40. A process accordingly to claim 39, wherein said human keratin fibres are hair.

41. A process according to claim 32, wherein said at least one oxidizing agent is chosen from hydrogen peroxide, urea peroxide, alkali metal bromates, persalts, peracids and enzymes.

42. A process according to claim 41, wherein said persalts are chosen from perborates and persulphates.

43. A process according to claim 41, wherein said enzymes are chosen from peroxidases, laccases, tyrosinases and oxidoreductases.

44. A process according to claim 43, wherein said oxidoreductases are chosen from pyranose oxidase, glucose oxidase, glycerol oxidase, lactate oxidase, pyruvate oxidase and uricase.

45. A process according to claim 35, wherein said at least one oxidizing agent is chosen from hydrogen peroxide, urea peroxide, alkali metal bromates, persalts, peracids and enzymes.

46. A process according to claim 45, wherein said persalts are chosen from perborates and persulphates.

47. A process according to claim 46, wherein said enzymes are chosen from peroxidases, laccases, tyrosinases and oxidoreductases.

48. A process according to claim 47, wherein said oxidoreductases are chosen from pyranose oxidase, glucose oxidase, glycerol oxidase, lactate oxidase, pyruvate oxidase and uricase.

49. A process according to claim 28, wherein said sufficient time to develop a desired color ranges from 3 minutes to 50 minutes.

50. A process according to claim 49, wherein said sufficient time to develop a desired color ranges from 5 minutes to 30 minutes.

51. A process according to claim 28, further comprising rinsing said keratin fibres.

52. A process according to claim 51, further comprising washing said keratin fibres with shampoo.

53. A process according to claim 52, further comprising rinsing and drying said keratin fibres.

54. A process according to claim 38, wherein the pH of said at least one oxidizing composition mixed with said at least one dye composition ranges from 3 to 12.

55. A process according to claim 54, wherein the pH of said at least one oxidizing composition mixed with said at least one dye composition ranges from 5 to 11.

56. A multicompartment device or kit for oxidation dyeing of keratin fibres comprising a first compartment containing a first composition comprising, in a medium suitable for dyeing, (i) at least one oxidation base and (ii) at least one coupler chosen from indolizine derivatives of formula (I) and the acid addition salts thereof:

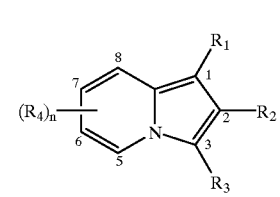

(I)

wherein:
n may be an integer from 0 to 4;
$R_1$ and $R_3$, which may be identical or different, are each chosen from hydrogen atoms; halogen atoms; Z groups; $C_1$–$C_4$ alkyl radicals; $C_1$–$C_4$ alkoxy radicals; $C_1$–$C_4$ monohydroxyalkyl radicals; $C_2$–$C_4$ polyhydroxyalkyl radicals; $C_1$–$C_4$ aminoalkyl radicals; acetylamino radicals; acetylamino-($C_1$–$C_4$)alkyl radicals; ($C_1$–$C_4$)alkoxy($C_1$–$C_4$)alkyl radicals; mono($C_1$–$C_4$)alkylamino($C_1$–$C_4$)alkyl radicals; di($C_1$–$C_4$)alkylamino($C_1$–$C_4$)alkyl radicals; aminocarboxy($C_1$–$C_4$)alkyl radicals; acetyl($C_1$–$C_4$)alkylamino ($C_1$–$C_4$)alkyl radicals; and aromatic rings which are optionally substituted with at least one radical chosen from halogen atoms, $C_1$–$C_4$ alkyl radicals, trifluoromethyl radicals, $C_1$–$C_4$ alkoxy radicals, amino radicals, mono- and disubstituted amino radicals wherein the substituent is chosen from $C_1$–$C_4$ alkyl radicals, $(C_1$–$C_4)$alkylamino$(C_1$–$C_4)$alkyl radicals, di$(C_1$–$C_4)$alkylamino$(C_1$–$C_4)$alkyl radicals, carboxyl radicals and sulphoxy radicals;

$R_3$ may optionally further be chosen from 5- and 6-membered unsaturated heterocycles;

$R_2$ and $R_4$, which may be identical or different, are each chosen from hydrogen atoms; halogen atoms, Z groups; $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, mono$(C_1$–$C_4)$-alkylamino$(C_1$–$C_4)$ alkyl radicals, di$(C_1$–$C_4)$alkyl-amino$(C_1$–$C_4)$alkyl radicals, carboxyl radicals, cyano radicals, carboxy$(C_1$–$C_4)$alkyl radicals, nitro radicals and 5- and 6-membered aromatic rings which are optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, $(C_1$–$C_4)$alkylamino-$(C_1$–$C_4)$alkyl radicals, di$(C_1$–$C_4)$alkylamino-$(C_1$–$C_4)$alkyl radicals, carboxyl radicals and sulphoxy radicals;

Z is chosen from the following unsaturated cationic groups of formulae (II) and (III) below, and the saturated cationic groups of formula (IV) below:

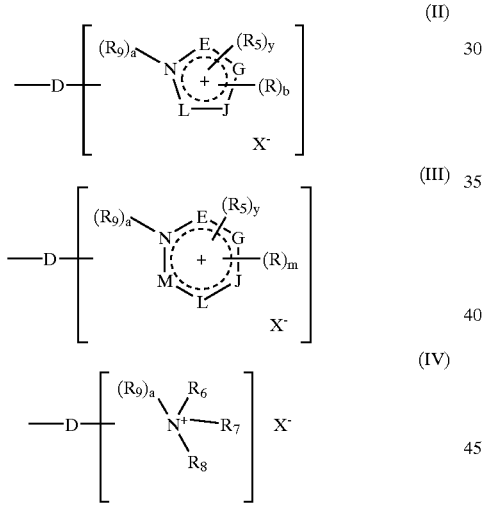

in which:

D is a linker arm which is chosen from linear and branched alkylene chains which may be interrupted by at least one hetero atom, and which may be substituted with at least one substituent chosen from hydroxyl and $C_1$–$C_6$ alkoxy radicals, and which may bear at least one ketone function;

the ring members E, G, J, L and M, which may be identical or different, are chosen from carbon, oxygen, sulphur and nitrogen atoms;

b is an integer from 0 to 4;

m is an integer from 0 to 5;

the radicals R, which may be identical or different, are chosen from a second group Z, which may be identical to or different from the first group Z, halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano$(C_1$–$C_6)$ alkyl radicals, $C_1$–$C_6$ alkoxy radicals, tri$(C_1$–$C_6)$ alkylsilane$(C_1$–$C_6)$alkyl radicals, amido radicals, aldehydo radicals, carboxyl radicals, $(C_1$–$C_6)$alkylcarbonyl radicals, thio radicals, $C_1$–$C_6$ thioalkyl radicals, $C_1$–$C_6$ alkylthio radicals, amino radicals, amino radicals protected with at least one group chosen from $(C_1$–$C_6)$ alkylcarbonyls, carbamyls and $C_1$–$C_6$ alkylsulphonyl radicals; NHR" and NR"R'" groups in which R" and R'", which may be identical or different, are chosen from $C_1$–$C_6$ alkyl radicals, $C_1$–$C_6$ monohydroxyalkyl radicals and $C_2$–$C_6$ polyhydroxyalkyl radicals;

$R_5$ is chosen from $C_1$–$C_6$ alkyl radicals, $C_1$–$C_6$ monohydroxyalkyl radicals, $C_2$–$C_6$ polyhydroxyalkyl radicals, cyano$(C_1$–$C_6)$alkyl radicals, tri$(C_1$–$C_6)$-alkylsilane$(C_1$–$C_6)$alkyl radicals, $(C_1$–$C_6)$alkoxy-$(C_1$–$C_6)$alkyl radicals, carbamyl$(C_1$–$C_6)$alkyl radicals, $(C_1$–$C_6)$alkylcarboxy$(C_1$–$C_6)$alkyl radicals, benzyl radicals and second Z groups which may be identical to or different from the first Z groups;

$R_6$, $R_7$ and $R_8$, which may be identical or different, are each chosen from $C_1$–$C_6$ alkyl radicals, $C_1$–$C_6$ monohydroxyalkyl radicals, $C_2$–$C_6$ polyhydroxyalkyl radicals, $(C_1$–$C_6)$alkoxy$(C_1$–$C_6)$alkyl radicals, cyano $(C_1$–$C_6)$alkyl radicals, aryl radicals, benzyl radicals, amido$(C_1$–$C_6)$alkyl radicals, tri$(C_1$–$C_6)$alkylsilane $(C_1$–$C_6)$alkyl radicals and $C_1$–$C_6$ aminoalkyl radicals in which the amine is protected with at least one group chosen from $(C_1$–$C_6)$alkylcarbonyls, carbamyls and $C_1$–$C_6$ alkylsulphonyl radicals; two of the radicals $R_6$, $R_7$ and $R_8$, may also form, together with the nitrogen atom to which they are attached, 5- and 6-membered saturated carbon-based rings and rings containing at least one hetero atom, it being possible for the said ring to be optionally substituted with at least one substituent chosen from halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano$(C_1$–$C_6)$alkyl radicals, $C_1$–$C_6$ alkoxy radicals, tri$(C_1$–$C_6)$alkylsilane$(C_1$–$C_6)$alkyl radicals, amido radicals, aldehydo radicals, carboxyl radicals, keto$(C_1$–$C_6)$alkyl radicals, thio radicals, $C_1$–$C_6$ thioalkyl radicals, $C_1$–$C_6$ alkylthio radicals, amino radicals and amino radical protected with at least one group chosen from $(C_1$–$C_6)$alkylcarbonyls, carbamyls and $C_1$–$C_6$ alkylsulphonyl radicals;

one of the radicals $R_6$, $R_7$ and $R_8$ may optionally be chosen from second Z groups, which may be identical to or different from the first Z groups;

$R_9$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is protected by at least one group chosen from $(C_1$–$C_6)$ alkylcarbonyls, carbamyls and $C_1$–$C_6$ alkylsulphonyl radicals; carboxy$(C_1$–$C_6)$alkyl radicals; cyano$(C_1$–$C_6)$ alkyl radicals; carbamyl$(C_1$–$C_6)$alkyl radicals; $C_1$–$C_6$ trifluoroalkyl radicals; tri$(C_1$–$C_6)$alkylsilane$(C_1$–$C_6)$ alkyl radicals; sulphonamido$(C_1$–$C_6)$alkyl radicals; $(C_1$–$C_6)$alkylcarboxy$(C_1$–$C_6)$alkyl radicals; $(C_1$–$C_6)$ alkylsulphinyl$(C_1$–$C_6)$alkyl radicals; $(C_1$–$C_6)$ alkylsulphonyl$(C_1$–$C_6)$alkyl radicals; $(C_1$–$C_6)$ alkylketo$(C_1$–$C_6)$alkyl radicals; N-$(C_1$–$C_6)$ alkylcarbamyl$(C_1$–$C_6)$alkyl radicals; and N-$(C_1$–$C_6)$ alkylsulphonamido$(C_1$–$C_6)$alkyl radicals;

a and y are integers equal to 0 or 1; with the following provisos:

in the unsaturated cationic groups of formula (II):
  when a=0, the linker arm D is attached to the nitrogen atom,
  when a=1, the linker arm D is attached to one of the ring members E, G, J and L,
  y cannot take the value 1 except:
    1) when the ring members E, G, J and L simultaneously represent a carbon atom, and when the radical $R_5$ is attached to the nitrogen atom of the unsaturated ring; or alternatively
    2) when at least one of the ring members E, G, J and L represents a nitrogen atom to which the radical $R_5$ is attached;
  when b is at least 2, two adjacent radicals R may also form together a ring chosen from unsaturated 5- and 6-membered carbon-based rings and rings containing at least one hetero atom;
in the unsaturated cationic groups of formula (III):
  when a=0, the linker arm D is attached to the nitrogen atom,
  when a=1, the linker arm D is attached to one of the ring members E, G, J, L and M,
  y cannot take the value 1 except when at least one of the ring members E, G, J, L and M represents a divalent atom, and when the radical $R_5$ is attached to the nitrogen atom of the unsaturated ring;
  when m is at least 2, two adjacent radicals R may also form together unsaturated 5- and 6-membered carbon-based rings and rings containing at least one hetero atom;
in the cationic groups of formula (IV):
  when a=0, the linker arm D is attached to the nitrogen atom bearing the radicals $R_6$ to $R_8$,
  when a=1, two of the radicals $R_6$ to $R_8$ form, together with the nitrogen atom to which they are attached, saturated 5- and 6-membered rings as defined above, and the linker arm D is attached to a carbon atom of the said saturated ring;
$X^-$ is chosen from monovalent and divalent anions;
it being understood that:
  at least one of the radicals $R_1$ and $R_3$ represents a hydrogen atom; and
  wherein at least one of R1, R2, R3 or R4 is a Z group;
and a second compartment containing at least one oxidizing composition.

57. The composition according to claim 56, wherein said linker arm D is chosen from linear and branched alkylene chains containing from 1 to 14 carbon atoms.

58. A compound chosen from indolizine derivatives of formula (I), and acid addition salts thereof,

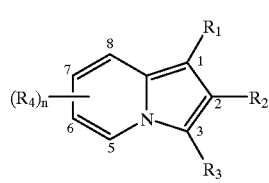

(I)

wherein:
  n may be an integer from 0 to 4;
  $R_1$ and $R_3$, which may be identical or different, are each chosen from hydrogen atoms; halogen atoms; Z groups; $C_1$–$C_4$ alkyl radicals; $C_1$–$C_4$ alkoxy radicals; $C_1$–$C_4$ monohydroxyalkyl radicals; $C_2$–$C_4$ polyhydroxyalkyl radicals; $C_1$–$C_4$ aminoalkyl radicals; acetylamino radicals; acetylamino-($C_1$–$C_4$)alkyl radicals; ($C_1$–$C_4$)alkoxy($C_1$–$C_4$)alkyl radicals; mono($C_1$–$C_4$)alkylamino($C_1$–$C_4$)alkyl radicals; di($C_1$–$C_4$)alkylamino($C_1$–$C_4$)alkyl radicals; aminocarboxy ($C_1$–$C_4$)alkyl radicals; acetyl($C_1$–$C_4$)alkylamino ($C_1$–$C_4$)alkyl radicals; and aromatic rings which are optionally substituted with at least one radical chosen from halogen atoms, $C_1$–$C_4$ alkyl radicals, trifluoromethyl radicals, $C_1$–$C_4$ alkoxy radicals, amino radicals, mono- and disubstituted amino radicals wherein the substituent is chosen from $C_1$–$C_4$ alkyl radicals, ($C_1$–$C_4$)alkylamino($C_1$–$C_4$)alkyl radicals, di($C_1$–$C_4$)alkylamino($C_1$–$C_4$)alkyl radicals, carboxyl radicals and sulphoxy radicals;

$R_3$ may optionally further be chosen from 5- and 6-membered unsaturated heterocycles;

$R_2$ and $R_4$, which may be identical or different, are each chosen from hydrogen atoms; halogen atoms, Z groups; $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, mono($C_1$–$C_4$)-alkylamino($C_1$–$C_4$) alkyl radicals, di($C_1$–$C_4$)alkyl-amino($C_1$–$C_4$)alkyl radicals, carboxyl radicals, cyano radicals, carboxy ($C_1$–$C_4$)alkyl radicals, nitro radicals and 5- and 6-membered aromatic rings which are optionally substituted with at least one radical chosen from halogen atoms, $C_1$–$C_4$ alkyl radicals, trifluoromethyl radicals, $C_1$–$C_4$ alkoxy radicals, amino radicals and mono- and disubstituted amino radicals wherein the substituent is chosen from $C_1$–$C_4$ alkyl radicals, ($C_1$–$C_4$)alkylamino-($C_1$–$C_4$)alkyl radicals, di($C_1$–$C_4$)alkylamino-($C_1$–$C_4$) alkyl radicals, carboxyl radicals and sulphoxy radicals;

Z is chosen from the following unsaturated cationic groups of formulae (II) and (III) below, and the saturated cationic groups of formula (IV) below:

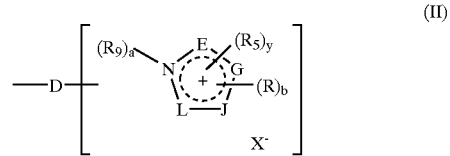

(II)

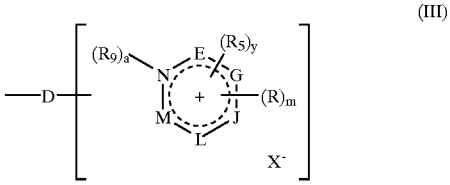

(III)

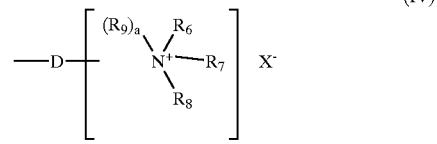

(IV)

in which:
  D is a linker arm which is chosen from linear and branched alkylene chains which may be interrupted by at least one hetero atom, and which may be substituted with at least one substituent chosen from hydroxyl and $C_1$–$C_6$ alkoxy radicals, and which may bear at least one ketone function;
  the ring members E, G, J, L and M, which may be identical or different, are chosen from carbon, oxygen, sulphur and nitrogen atoms;

b is an integer from 0 to 4;

m is an integer from 0 to 5;

the radicals R, which may be identical or different, are chosen from a second group Z, which may be identical to or different from the first group Z, halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$) alkyl radicals, $C_1$–$C_6$ alkoxy radicals, tri($C_1$–$C_6$)alkylsilane($C_1$–$C_6$)alkyl radicals, amido radicals, aldehydo radicals, carboxyl radicals, ($C_1$–$C_6$)alkylcarbonyl radicals, thio radicals, $C_1$–$C_6$ thioalkyl radicals, $C_1$–$C_6$ alkylthio radicals, amino radicals, amino radicals protected with at least one group chosen from ($C_1$–$C_6$) alkylcarbonyls, carbamyls and $C_1$–$C_6$ alkylsulphonyl radicals; NHR" and NR"R"' groups in which R" and R"', which may be identical or different, are chosen from $C_1$–$C_6$ alkyl radicals, $C_1$–$C_6$ monohydroxyalkyl radicals and $C_2$–$C_6$ polyhydroxyalkyl radicals; $R_5$ is chosen from $C_1$–$C_6$ alkyl radicals, $C_1$–$C_6$ monohydroxyalkyl radicals, $C_2$–$C_6$ polyhydroxyalkyl radicals, cyano($C_1$–$C_6$)alkyl radicals, tri($C_1$–$C_6$)-alkylsilane($C_1$–$C_6$)alkyl radicals, ($C_1$–$C_6$)alkoxy-($C_1$–$C_6$)alkyl radicals, carbamyl($C_1$–$C_6$)alkyl radicals, ($C_1$–$C_6$)alkylcarboxy($C_1$–$C_6$)alkyl radicals, benzyl radicals and second Z groups which may be identical to or different from the first Z groups;

$R_6$, $R_7$ and $R_8$, which may be identical or different, are each chosen from $C_1$–$C_6$ alkyl radicals, $C_1$–$C_6$ monohydroxyalkyl radicals, $C_2$–$C_6$ polyhydroxyalkyl radicals, ($C_1$–$C_6$)alkoxy($C_1$–$C_6$)alkyl radicals, cyano ($C_1$–$C_6$)alkyl radicals, aryl radicals, benzyl radicals, amido($C_1$–$C_6$)alkyl radicals, tri($C_1$–$C_6$)alkylsilane ($C_1$–$C_6$)alkyl radicals and $C_1$–$C_6$ aminoalkyl radicals in which the amine is protected with at least one group chosen from ($C_1$–$C_6$)alkylcarbonyls, carbamyls and $C_1$–$C_6$ alkylsulphonyl radicals; two of the radicals $R_6$, $R_7$ and $R_8$, may also form, together with the nitrogen atom to which they are attached, 5- and 6-membered saturated carbon-based rings and rings containing at least one hetero atom, it being possible for the said ring to be optionally substituted with at least one substituent chosen from halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, nitro radicals, cyano radicals, cyano($C_1$–$C_6$)alkyl radicals, $C_1$–$C_6$ alkoxy radicals, tri($C_1$–$C_6$)alkylsilane($C_1$–$C_6$)alkyl radicals, amido radicals, aldehydo radicals, carboxyl radicals, keto($C_1$–$C_6$)alkyl radicals, thio radicals, $C_1$–$C_6$ thioalkyl radicals, $C_1$–$C_6$ alkylthio radicals, amino radicals and amino radical protected with at least one group chosen from ($C_1$–$C_6$)alkylcarbonyls, carbamyls and $C_1$–$C_6$ alkylsulphonyl radicals;

one of the radicals $R_6$, $R_7$ and $R_8$ may optionally be chosen from second Z groups, which may be identical to or different from the first Z groups;

$R_9$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is protected by at least one group chosen from ($C_1$–$C_6$) alkylcarbonyls, carbamyls and $C_1$–$C_6$ alkylsulphonyl radicals; carboxy($C_1$–$C_6$)alkyl radicals; cyano($C_1$–$C_6$) alkyl radicals; carbamyl($C_1$–$C_6$)alkyl radicals; $C_1$–$C_6$ trifluoroalkyl radicals; tri($C_1$–$C_6$)alkylsilane($C_1$–$C_6$) alkyl radicals; sulphonamido($C_1$–$C_6$)alkyl radicals; ($C_1$–$C_6$)alkylcarboxy($C_1$–$C_6$)alkyl radicals; ($C_1$–$C_6$) alkylsulphinyl($C_1$–$C_6$)alkyl radicals; ($C_1$–$C_6$) alkylsulphonyl($C_1$–$C_6$)alkyl radicals; ($C_1$–$C_6$) alkylketo($C_1$–$C_6$)alkyl radicals; N-($C_1$–$C_6$) alkylcarbamyl($C_1$–$C_6$)alkyl radicals; and N-($C_1$–$C_6$) alkylsulphonamido($C_1$–$C_6$)alkyl radicals;

a and y are integers equal to 0 or 1; with the following provisos:

in the unsaturated cationic groups of formula (II):
when a=0, the linker arm D is attached to the nitrogen atom,
when a=1, the linker arm D is attached to one of the ring members E, G, J and L,
y cannot take the value 1 except:
1) when the ring members E, G, J and L simultaneously represent a carbon atom, and when the radical $R_5$ is attached to the nitrogen atom of the unsaturated ring; or alternatively
2) when at least one of the ring members E, G, J and L represents a nitrogen atom to which the radical $R_5$ is attached;
when b is at least 2, two adjacent radicals R may also form together a ring chosen from unsaturated 5- and 6-membered carbon-based rings and rings containing at least one hetero atom;

in the unsaturated cationic groups of formula (III):
when a=0, the linker arm D is attached to the nitrogen atom,
when a=1, the linker arm D is attached to one of the ring members E, G, J, L and M,
y cannot take the value 1 except when at least one of the ring members E, G, J, L and M represents a divalent atom, and when the radical $R_5$ is attached to the nitrogen atom of the unsaturated ring;
when m is at least 2, two adjacent radicals R may also form together unsaturated 5- and 6-membered carbon-based rings and rings containing at least one hetero atom;

in the cationic groups of formula (IV):
when a=0, the linker arm D is attached to the nitrogen atom bearing the radicals $R_6$ to $R_8$,
when a=1, two of the radicals $R_6$ to $R_8$ form, together with the nitrogen atom to which they are attached, saturated 5- and 6-membered rings as defined above, and the linker arm D is attached to a carbon atom of the said saturated ring;

$X^-$ is chosen from monovalent and divalent anions;

with the following provisos:
at least one of the radicals $R_1$ and $R_3$ represents a hydrogen atom; and
wherein at least one of R1, R2, R3 or R4 is a Z group;
Z cannot be chosen from the cationic groups of formula (IV); and
4-methyl-4-[2-(2-phenyl-1-indolizinyl)ethyl] morpholinium bromide is excluded.

59. The composition according to claim 58, wherein said linker arm D is chosen from linear and branched alkylene chains containing from 1 to 14 carbon atoms.

60. The compound according to claim 58, wherein said compound is chosen from:

1-methyl-2-[2-(7-methyl-2-phenylindolizin-3-yl)ethyl] pyridinium methyl sulphate;

3-methyl-1-[2-(7-methyl-2-phenylindolizin-3-yl)-2-oxoethyl]-3H-imidazol-1-ium chloride;

3-methyl-1-[2-(2-methylindolizin-3-yl)-2-oxoethyl]-3H-imidazol-1-ium chloride;

1-{2-[2-(4-methoxyphenyl)-8-methylindolizin-3-yl]-2-oxoethyl}-3-methyl-3H-imidazol-1-ium chloride;

3-methyl-1-{2-[8-methyl-2-(3-nitrophenyl)indolizin-3-yl]-2-oxoethyl}-3H- imidazol-1-ium chloride;
1-{2-[2-(3-nitrophenyl)indolizin-3-yl]-2-oxoethyl}pyridinium chloride;
1-[2-oxo-2-(2-phenylindolizin-3-yl)ethyl]pyridinium chloride;
1-[2-oxo-2-(2-m-tolylindolizin-3-yl)ethyl]pyridinium chloride;
1-[2-(8,1-{2-[2-(4-methoxyphenyl)-8-methylindolizin-3-yl]-2-oxoethyl}-2-methylpyridinium chloride;
2-phenylindolizin-3-yl)-2-oxoethyl]pyridinium methyl chloride;
[2-(8-methyl-2-phenylindolizin-3-yl)-2-oxoethyl] pyridinium chloride;
2-methyl-1-{2-[2-(3-nitrophenyl)indolizin-3-yl]-2-oxoethyl}pyridinium chloride;
2-methyl-1-[2-oxo-2-(2-phenylindolizin-3-yl)ethyl]pyridinium chloride;
2-methyl-1-{2-[8-methyl-2-(3-nitrophenyl)indolizin-3-yl]-2-oxoethyl}pyrid in ium chloride;
2-methyl-1-[2-(8-methyl-2-phenylindolizin-3-yl)-2-oxoethyl]pyridinium chloride;
3-methoxycarbonyl-1-{2-[2-(3-nitrophenyl)indolizin-3-yl]-2-oxoethyl}pyridinium chloride;
3-methoxycarbonyl-1-[2-oxo-2-(2-phenylindolizin-3-yl)ethyl]pyridinium chloride;
3-methoxycarbonyl-1-{2-[2-(4-methoxyphenyl)-8-methylindolizin-3-yl]-2-oxoethyl}pyridinium chloride;
3-methoxycarbonyl-1-{2-[8-methyl-2-(3-nitrophenyl)indolizin-3-yl]-2-oxoethyl}pyridinium chloride;
3-methoxycarbonyl-1-[2-(8-methyl-2-phenylindolizin-3-yl)-2-oxoethyl]pyridinium chloride; and the addition salts thereof with an acid.

61. The composition according to claim 9, wherein the heterocyclic bases are chosen from pyridine derivatives, pyrimidine derivatives and pyrazole derivatives, and the acid addition salts thereof.

* * * * *

UNITED STATES PATENT AND TRADEMARK OFFICE
CERTIFICATE OF CORRECTION

PATENT NO. : 6,579,326 B2  Page 1 of 2
DATED : June 17, 2003
INVENTOR(S) : Philippe Breton et al.

It is certified that error appears in the above-identified patent and that said Letters Patent is hereby corrected as shown below:

Column 20,
Line 5, "X- is" should read -- $X^-$ is --.
Line 8, "(wherein" should read -- wherein --.
Lines 16-17, "4-methyl-4-[2-(2-phenyl-1-indolizinyl )ethyl]morpholinium bromide;" should read -- 4-methyl-4-[2-(2-phenyl-1-indolizinyl)ethyl]morpholinium bromide; --.
Lines 27-28, "trimethyl[2-(2-phenyl-1 -indolizinly)ethyl]ammonium bromide;" should read -- trimethyl[2-(2-phenyl-1-indolizinly)ethyl]ammonium bromide; --.
Lines 38-39, "3-methyl-1-{2-[8-methyl-2-(3-nitrophenyl)indolizin-3-yl]-2-oxoethyl}- 3 H-imidazol-1-ium chloride;" should read -- 3-methyl-1-{2-[8-methyl-2-(3-nitrophenyl) indolizin-3-yl]-2-oxoethyl}-3H-imidazol-1-ium chloride; --.
Lines 49-50, "2-phenylindolizin-3-yl )-2-oxoethyl]pyridinium methyl chloride;" should read -- 2-phenylindolizin-3-yl)-2-oxoethyl]pyridinium methyl chloride; --.
Lines 62-63, "3-methoxycarbonyl-1-{2-[2-(3-nitropheny)indolizin-3-yl]-2-oxoethyl} pyridinium chloride;" should read -- 3-methoxycarbonyl-1-{2-[2-(3-nitrophenyl) indolizin-3-yl]-2-oxoethyl}pyridinium chloride --.
Lines 64-65, "3-methoxycarbonyl-1-[2-oxo-2-(2-phenylindolizin-3-yl )ethyl]pyridinium chloride;" should read -- 3-methoxycarbonyl-1-[2-oxo-2-(2-phenylindolizin-3-ly)ethyl] pyridinium chloride; --.
Lines 66-67, "3-methoxycarbonyl-1-{2-[2-(4-methoxyphenyl )-8-methylindolizin-3-yl]-2-oxoethyl}pyridinium chloride;" should read -- 3-methoxycarbonyl-1-{2-(4-methoxyphenyl)-8-methylindolizin-3-yl]-2-oxoethyl}pyridinium chloride; --.

Column 21,
Lines 1-2, "3-methoxycarbonyl-1-{2-[2-(3-nitrophenyl)indolizin-3-yl]-2-oxoethyl} pyridinium chloride;" should read -- 3-methoxycarbonyl-1-{2-[8-methyl-2-(3-nitrophenyl)indolizin-3-yl]-2-oxoethyl}pyridinium chloride; --.
Line 55, "bromides" should read -- bromide, --.

Column 23,
Lines 13-14, "N,N'-bis(p-hydroxyethyl)-N,N'-bis(4-aminophenyl) tetramethylenediamine," should read -- N,N'-bis(β-hydroxyethyl)-N,N'-bis(4-aminophenyl)tetramethylenediamine, --.
Lines 14-15, "N,N'-bis(4-methylaminophenyl )tetramethylenediamine," should read -- N,N'-bis(4-methylaminophenyl)tetramethylenediamine, --.
Lines 55-56, "4-amino-2-methyl phenol," should read -- 4-amino-2-methylphenol, --.

UNITED STATES PATENT AND TRADEMARK OFFICE
CERTIFICATE OF CORRECTION

PATENT NO. : 6,579,326 B2
DATED : June 17, 2003
INVENTOR(S) : Philippe Breton et al.

It is certified that error appears in the above-identified patent and that said Letters Patent is hereby corrected as shown below:

Column 25,
Line 62, "NHR'" should read -- NHR" --.

Column 27,
Line 57, "accordingly to" should read -- according to --.

Column 28,
Line 11, "claim 46," should read -- claim 45, --.

Column 35,
Lines 1-2, "3-methyl-1-{2-[8-methyl-2-(3-nitrophenyl)indolizin-3-yl]-2-oxoethyl}-3H-imidazol-1-ium chloride;" should read -- 3-methyl-1-{2-[8-methyl-2-(3-nitrophenyl)indolizin-3-yl]-2-oxoethyl}-3H-imidazol-1-ium chloride; --.
Lines 14-15, "[2-(8-methyl-2-phenylindolizin-3-yl)-2-oxoethyl] pyridinium chloride;" should read -- [2-(8-methyl-2-phenylindolizin-3-yl)-2-oxoethyl]pyridinium chloride; --.
Lines 21-22, "2-methyl-1-{2-[8-methyl-2-(3-nitrophenyl)indolizin-3-yl]-2-oxoethyl}pyrid in ium chloride;" should read -- 2-methyl-1-{2-[8-methyl-2-(3-nitrophenyl)indolizin-3-yl]-2-oxoethyl}pyridinium chloride; --.

Signed and Sealed this

Seventeenth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,579,326 B2
DATED : June 17, 2003
INVENTOR(S) : Philippe Breton et al.

It is certified that error appears in the above-identified patent and that said Letters Patent is hereby corrected as shown below:

Column 20,
Lines 27-28, "trimethyl[2-(2-phenyl-1-indolizinly)ethyl]ammonium bromide;" should read -- trimethyl[2-(2-phenyl-1-indolizinyl)ethyl]ammonium bromide; --.
Lines 64-65, "3-methoxycarbonyl-1-[2-oxo-2-(2-phenylindolizin-3-ly)ethyl]pyridinium chloride;" should read -- 3-methoxycarbonyl-1-[2-oxo-2-(2-phenylindolizin-3-yl]ethyl]pyridinium chloride; --.
Lines 66-67, "3-methoxycarbonyl-1-{2-(4-methoxyphenyl)-8-methylindolizin-3-yl]-2-oxoethy}pyridinium chloride;" should read -- 3-methoxycarbonyl-1-{2-[2-(4-methoxy-phenyl)-8-methylindolizin-3-yl]-2-oxoethyl}pyridinium chloride; --.

Signed and Sealed this

Eleventh Day of May 2004

JON W. DUDAS
*Acting Director of the United States Patent and Trademark Office*